Figure 1:
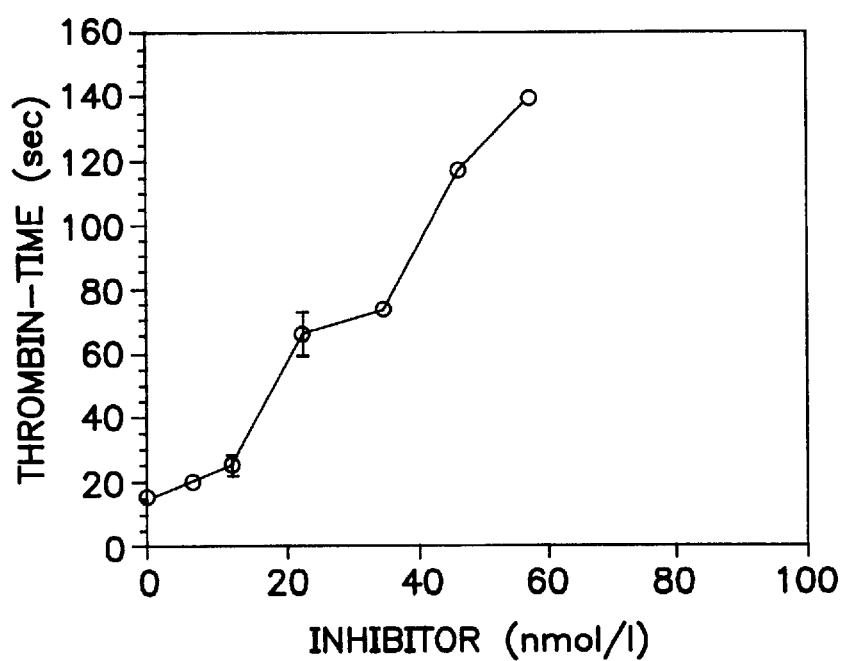

United States Patent [19]
Noeske-Jungblut et al.

[11] Patent Number: 5,876,971
[45] Date of Patent: Mar. 2, 1999

[54] THROMBIN INHIBITOR FROM THE SALIVA OF PROTOSTOMIA

[75] Inventors: Christiane Noeske-Jungblut; Wolf-Dieter Schleuning, both of Berlin, Germany; Alejandro Alagon, Cuernavaca, Mexico; Lourival Possani, Cuernavaca, Mexico; Delia Cuevas-Aguierre, Cuernavaca, Mexico; Peter Donner, Berlin, Germany; Bernard Haendler, Berlin, Germany; Ulrike Hechler, Berlin, Germany

[73] Assignee: Schering Aktiengesellschaft, Germany

[21] Appl. No.: 448,438

[22] PCT Filed: Dec. 3, 1993

[86] PCT No.: PCT/DE93/01172

§ 371 Date: Aug. 24, 1995

§ 102(e) Date: Aug. 24, 1995

[87] PCT Pub. No.: WO94/13807

PCT Pub. Date: Jun. 23, 1994

Related U.S. Application Data

[63] Continuation of Ser. No. 460,383, Jun. 2, 1995, abandoned.

[30] Foreign Application Priority Data

Dec. 4, 1992 [DE] Germany .......................... 42 41 659.0
Feb. 12, 1993 [DE] Germany .......................... 43 04 731.9
Aug. 17, 1993 [DE] Germany .......................... 43 28 336.5
Nov. 25, 1993 [DE] Germany .......................... 43 40 798.6

[51] Int. Cl.$^6$ .......................... C12P 21/02; C07K 14/435; C07K 1/36; A61K 38/16

[52] U.S. Cl. .................. 435/69.1; 435/252.3; 435/320.1; 514/12; 530/324; 530/412

[58] Field of Search ................ 435/69.1, 320.1, 435/252.3; 514/12; 530/324, 412, 413

[56] References Cited

PUBLICATIONS

Hoffman, A. et al. (Mar. 1991) "Isolation and characterization of a thrombin inhibitor from the tick *Ixodes ricinus*" Pharmazie 46(3):209–212.

*Primary Examiner*—Kawai Lau
*Attorney, Agent, or Firm*—Millen, White, Zelano & Branigan, P.C.

[57] ABSTRACT

The invention relates to a natural protein or a protein that can be synthetically produced, which is a thrombin inhibitor and can be isolated from the saliva of insects which suck the blood of mammals. Preferred is the *Triatoma pallidipennis* insect. The protein is used for the treatment of thromboses or unstable angina or arteriosclerosis, or for the prevention of a reblockage of vessels after PTCA/PTA or for the prevention of blood clotting in hemodialysis.

29 Claims, 3 Drawing Sheets

SEQUENCE LISTING ( 1 ) GENERAL INFORMATION:

( i i i ) NUMBER OF SEQUENCES: 29

( 2 ) INFORMATION FOR SEQ ID NO: 1:

( i ) SEQUENCE CHARACTERISTICS:
        ( A ) LENGTH: 142 amino acids
        ( B ) TYPE: amino acid sequence
        ( C ) STRANDEDNESS: single
        ( D ) TOPOLOGY: linear ( i i ) MOLECULE TYPE: protein ( v i ) ORIGINAL SOURCE:
        ( A ) ORGANISM: SALIVA GLAND OF TRIATOMA PALLIDIPENNIS
        ( C ) INDIVIDUAL ISOLATE: Ti 12

( x i ) SEQUENCE DESCRIPTION: SEQ ID NO: 1:

```
Ala  Glu  Gly  Asp  Asp  Cys  Ser  Leu  Glu  Lys  Ala  Met  Gly  Asp  Phe  Lys
 1              5                        10                       15

Pro  Glu  Glu  Phe  Phe  Asn  Gly  Thr  Trp  Tyr  Leu  Ala  His  Gly  Pro  Gly
              20                        25                       30

Val  Thr  Ser  Pro  Ala  Val  Cys  Gln  Lys  Phe  Thr  Thr  Ser  Gly  Ser  Lys
              35                        40                       45
```

|     |     |     |     |     |     |     |     |     |     |     |     |     |     |     |
|-----|-----|-----|-----|-----|-----|-----|-----|-----|-----|-----|-----|-----|-----|-----|
| Gly | Phe 50 | Thr | Gln | Ile | Val | Glu 55 | Ile | Gly | Tyr | Asn | Lys 60 | Phe | Glu | Ser | Asn |
| Val 65 | Lys | Phe | Gln | Cys | Asn 70 | Gln | Val | Asp | Asn | Lys 75 | Asn | Asp | Glu | Gln | Tyr 80 |
| Ser | Phe | Lys | Cys | Lys 85 | Gly | Ser | Asp | Asn | Thr 90 | Glu | Phe | Glu | Ala | Asp 95 | Phe |
| Thr | Phe | Ile | Ser 100 | Val | Ser | Tyr | Asp | Asn 105 | Phe | Ala | Leu | Val | Cys 110 | Arg | Ser |
| Ile | Ile | Phe 115 | Thr | Ser | Gln | Pro | Lys 120 | Glu | Asp | Asp | Tyr | Leu 125 | Val | Phe | Glu |
| Arg | Thr 130 | Lys | Ser | Asp | Thr | Asp 135 | Pro | Asp | Ala | Asn | Glu 140 | Ile | Cys |

( 2 ) INFORMATION FOR SEQ ID NO: 2:

( i ) SEQUENCE CHARACTERISTICS:
( A ) LENGTH: 142 amino acids
( B ) TYPE: amino acid sequence
( C ) STRANDEDNESS: single
( D ) TOPOLOGY: linear ( i i ) MOLECULE TYPE: protein ( v i ) ORIGINAL SOURCE:
( A ) ORGANISM: SALIVA GLAND OF TRIATOMA PALLIDIPENNIS
( C ) INDIVIDUAL ISOLATE: Ti 28

( x i ) SEQUENCE DESCRIPTION: SEQ ID NO: 2:

| Ala 1 | Glu | Gly | Asp | Asp 5 | Cys | Ser | Leu | Glu | Lys 10 | Ala | Met | Gly | Asp | Phe | Lys 15 |
| Pro | Glu | Glu | Phe 20 | Phe | Asn | Gly | Thr | Trp 25 | Tyr | Leu | Ala | His | Gly 30 | Pro | Asp |
| Val | Thr | Ser 35 | Pro | Ala | Val | Cys | Gln 40 | Lys | Phe | Thr | Thr | Ser 45 | Gly | Ser | Lys |
| Gly | Phe 50 | Thr | Gln | Ile | Val | Glu 55 | Ile | Gly | Tyr | Asn | Lys 60 | Phe | Glu | Ser | Asn |
| Val 65 | Lys | Phe | Gln | Cys | Asn 70 | Gln | Val | Asp | Asn | Lys 75 | Asn | Asp | Glu | Gln | Tyr 80 |
| Ser | Phe | Lys | Cys | Lys 85 | Gly | Ser | Asp | Asn | Thr 90 | Glu | Phe | Glu | Ala | Asp 95 | Phe |
| Thr | Phe | Ile | Ser 100 | Val | Ser | Tyr | Asp | Asn 105 | Phe | Ala | Leu | Val | Cys 110 | Arg | Ser |
| Ile | Ile | Phe 115 | Thr | Ser | Gln | Pro | Lys 120 | Glu | Asp | Asp | Tyr | Leu 125 | Val | Phe | Glu |
| Arg | Thr 130 | Lys | Ser | Asp | Thr | Asp 135 | Pro | Asp | Ala | Asn | Glu 140 | Ile | Cys |

( 2 ) INFORMATION FOR SEQ ID NO: 3:

( i ) SEQUENCE CHARACTERISTICS:
( A ) LENGTH: 142 amino acids
( B ) TYPE: amino acid sequence
( C ) STRANDEDNESS: single
( D ) TOPOLOGY: linear ( i i ) MOLECULE TYPE: protein ( v i ) ORIGINAL SOURCE:
( A ) ORGANISM: SALIVA GLAND OF TRIATOMA PALLIDIPENNIS
( C ) INDIVIDUAL ISOLATE: Ti 45

( x i ) SEQUENCE DESCRIPTION: SEQ ID NO: 3:

| Ala | Glu | Gly | Asp | Asp | Cys | Ser | Leu | Glu | Lys | Ala | Met | Gly | Asp | Phe | Lys |

|   | 1 |   |   | 5 |   |   |   |   | 10 |   |   |   |   | 15 |   |
|---|---|---|---|---|---|---|---|---|---|---|---|---|---|---|---|

```
Pro   Glu   Glu   Phe   Phe   Asn   Gly   Thr   Trp   Tyr   Leu   Ala   His   Gly   Pro   Asp
                  20                        25                        30

Val   Thr   Ser   Pro   Ala   Val   Cys   Gln   Lys   Phe   Thr   Thr   Ser   Gly   Ser   Lys
            35                        40                        45

Gly   Phe   Thr   Gln   Ile   Val   Glu   Ile   Gly   Tyr   Asn   Lys   Phe   Glu   Ser   Asn
      50                        55                        60

Val   Lys   Phe   Gln   Cys   Asn   Gln   Ala   Asp   Lys   Lys   Asn   Asp   Glu   Gln   Tyr
65                      70                        75                                    80

Ser   Phe   Lys   Cys   Lys   Gly   Ser   Asp   Asn   Thr   Glu   Phe   Glu   Ala   Asp   Phe
                        85                        90                              95

Thr   Phe   Ile   Ser   Val   Ser   Tyr   Asp   Asn   Phe   Ala   Leu   Val   Cys   Arg   Ser
                  100                       105                             110

Ile   Thr   Phe   Thr   Ser   Gln   Pro   Lys   Glu   Asp   Asp   Tyr   Leu   Val   Phe   Glu
            115                       120                             125

Arg   Thr   Lys   Ser   Asp   Thr   Asp   Pro   Asp   Ala   Asn   Glu   Ile   Cys
130                           135                       140
```

( 2 ) INFORMATION FOR SEQ ID NO: 4:

( i ) SEQUENCE CHARACTERISTICS:
            ( A ) LENGTH: 142 amino acids
            ( B ) TYPE: amino acid sequence
            ( C ) STRANDEDNESS: single
            ( D ) TOPOLOGY: linear ( i i ) MOLECULE TYPE: protein ( v i ) ORIGINAL SOURCE:
            ( A ) ORGANISM: SALIVA GLAND OF TRIATOMA PALLIDIPENNIS
            ( C ) INDIVIDUAL ISOLATE: Ti 5

( x i ) SEQUENCE DESCRIPTION: SEQ ID NO: 4:

```
Ala   Glu   Gly   Asp   Asp   Cys   Ser   Ile   Glu   Lys   Ala   Met   Gly   Asp   Phe   Lys
1                       5                         10                              15

Pro   Glu   Glu   Phe   Phe   Asn   Gly   Thr   Trp   Tyr   Leu   Ala   His   Gly   Pro   Gly
                  20                        25                        30

Val   Thr   Ser   Pro   Ala   Val   Cys   Gln   Lys   Phe   Thr   Thr   Ser   Gly   Ser   Lys
            35                        40                        45

Gly   Phe   Thr   Gln   Ile   Val   Glu   Ile   Gly   Tyr   Asn   Lys   Phe   Glu   Ser   Asn
      50                        55                        60

Val   Lys   Phe   Gln   Cys   Asn   Gln   Val   Asp   Asn   Lys   Asn   Gly   Glu   Gln   Tyr
65                      70                        75                                    80

Ser   Phe   Lys   Cys   Lys   Ser   Ser   Asp   Asn   Thr   Glu   Phe   Glu   Ala   Asp   Phe
                        85                        90                              95

Thr   Phe   Ile   Ser   Val   Ser   Tyr   Asp   Asn   Phe   Ala   Leu   Val   Cys   Arg   Ser
                  100                       105                             110

Ile   Thr   Phe   Thr   Ser   Gln   Pro   Lys   Glu   Asp   Asp   Tyr   Leu   Val   Leu   Glu
            115                       120                             125

Arg   Thr   Lys   Ser   Asp   Thr   Asp   Pro   Asp   Ala   Lys   Glu   Ile   Cys
130                           135                       140
```

( 2 ) INFORMATION FOR SEQ ID NO: 5:

( i ) SEQUENCE CHARACTERISTICS:
            ( A ) LENGTH: 160 amino acids
            ( B ) TYPE: amino acid sequence
            ( C ) STRANDEDNESS: single
            ( D ) TOPOLOGY: linear ( i i ) MOLECULE TYPE: protein ( v i ) ORIGINAL SOURCE:
    ( A ) ORGANISM: SALIVA GLAND OF TRIATOMA PALLIDIPENNIS
    ( C ) INDIVIDUAL ISOLATE: Ti 12

( i x ) FEATURE:
    ( A ) NAME/KEY: Protein
    ( B ) LOCATION: 19..160

( x i ) SEQUENCE DESCRIPTION: SEQ ID NO: 5:

| | | | | | | | | | | | | | | | |
|---|---|---|---|---|---|---|---|---|---|---|---|---|---|---|---|
| Met | Lys | Thr | Ile | Ile | Ala | Val | Thr | Ile | Phe | Gly | Ile | Leu | Thr | Cys | Ala |
| | | | -15 | | | | | -10 | | | | | -5 | | |
| Tyr | Ala | Ala | Glu | Gly | Asp | Asp | Cys | Ser | Leu | Glu | Lys | Ala | Met | Gly | Asp |
| | | 1 | | | | 5 | | | | | 10 | | | | |
| Phe | Lys | Pro | Glu | Glu | Phe | Phe | Asn | Gly | Thr | Trp | Tyr | Leu | Ala | His | Gly |
| 15 | | | | | 20 | | | | | 25 | | | | | 30 |
| Pro | Gly | Val | Thr | Ser | Pro | Ala | Val | Cys | Gln | Lys | Phe | Thr | Thr | Ser | Gly |
| | | | | 35 | | | | | 40 | | | | | 45 | |
| Ser | Lys | Gly | Phe | Thr | Gln | Ile | Val | Glu | Ile | Gly | Tyr | Asn | Lys | Phe | Glu |
| | | | 50 | | | | | 55 | | | | | 60 | | |
| Ser | Asn | Val | Lys | Phe | Gln | Cys | Asn | Gln | Val | Asp | Asn | Lys | Asn | Asp | Glu |
| | | 65 | | | | | 70 | | | | | 75 | | | |
| Gln | Tyr | Ser | Phe | Lys | Cys | Lys | Gly | Ser | Asp | Asn | Thr | Glu | Phe | Glu | Ala |
| | 80 | | | | | 85 | | | | | 90 | | | | |
| Asp | Phe | Thr | Phe | Ile | Ser | Val | Ser | Tyr | Asp | Asn | Phe | Ala | Leu | Val | Cys |
| 95 | | | | | 100 | | | | | 105 | | | | | 110 |
| Arg | Ser | Ile | Ile | Phe | Thr | Ser | Gln | Pro | Lys | Glu | Asp | Asp | Tyr | Leu | Val |
| | | | | 115 | | | | | 120 | | | | | 125 | |
| Phe | Glu | Arg | Thr | Lys | Ser | Asp | Thr | Asp | Pro | Asp | Ala | Asn | Glu | Ile | Cys |
| | | | 130 | | | | | 135 | | | | | 140 | | |

( 2 ) INFORMATION FOR SEQ ID NO: 6:

( i ) SEQUENCE CHARACTERISTICS:
( A ) LENGTH: 160 amino acids
( B ) TYPE: amino acid sequence
( C ) STRANDEDNESS: single
( D ) TOPOLOGY: linear ( i i ) MOLECULE TYPE: protein ( v i ) ORIGINAL SOURCE:
( A ) ORGANISM: SALIVA GLAND OF TRIATOMA PALLIDIPENNIS
( C ) INDIVIDUAL ISOLATE: Ti 28

( i x ) FEATURE:
( A ) NAME/KEY: Protein
( B ) LOCATION: 19..160

( x i ) SEQUENCE DESCRIPTION: SEQ ID NO: 6:

| | | | | | | | | | | | | | | | |
|---|---|---|---|---|---|---|---|---|---|---|---|---|---|---|---|
| Met | Lys | Thr | Ile | Ile | Ala | Val | Thr | Ile | Phe | Gly | Ile | Leu | Thr | Cys | Ala |
| | | | -15 | | | | | -10 | | | | | -5 | | |
| Tyr | Ala | Ala | Glu | Gly | Asp | Asp | Cys | Ser | Leu | Glu | Lys | Ala | Met | Gly | Asp |
| | | 1 | | | | 5 | | | | | 10 | | | | |
| Phe | Lys | Pro | Glu | Glu | Phe | Phe | Asn | Gly | Thr | Trp | Tyr | Leu | Ala | His | Gly |
| 15 | | | | | 20 | | | | | 25 | | | | | 30 |
| Pro | Asp | Val | Thr | Ser | Pro | Ala | Val | Cys | Gln | Lys | Phe | Thr | Thr | Ser | Gly |
| | | | | 35 | | | | | 40 | | | | | 45 | |
| Ser | Lys | Gly | Phe | Thr | Gln | Ile | Val | Glu | Ile | Gly | Tyr | Asn | Lys | Phe | Glu |
| | | | 50 | | | | | 55 | | | | | 60 | | |
| Ser | Asn | Val | Lys | Phe | Gln | Cys | Asn | Gln | Val | Asp | Asn | Lys | Asn | Asp | Glu |
| | | 65 | | | | | 70 | | | | | 75 | | | |

-continued

```
Gln  Tyr  Ser  Phe  Lys  Cys  Lys  Gly  Ser  Asp  Asn  Thr  Glu  Phe  Glu  Ala
     80                       85                       90

Asp  Phe  Thr  Phe  Ile  Ser  Val  Ser  Tyr  Asp  Asn  Phe  Ala  Leu  Val  Cys
95                       100                      105                      110

Arg  Ser  Ile  Ile  Phe  Thr  Ser  Gln  Pro  Lys  Glu  Asp  Asp  Tyr  Leu  Val
                    115                      120                      125

Phe  Glu  Arg  Thr  Lys  Ser  Asp  Thr  Asp  Pro  Asp  Ala  Asn  Glu  Ile  Cys
               130                      135                      140
```

( 2 ) INFORMATION FOR SEQ ID NO: 7:

( i ) SEQUENCE CHARACTERISTICS:
        ( A ) LENGTH: 160 amino acids
        ( B ) TYPE: amino acid sequence
        ( C ) STRANDEDNESS: single
        ( D ) TOPOLOGY: linear ( i i ) MOLECULE TYPE: protein ( v i ) ORIGINAL SOURCE:
        ( A ) ORGANISM: SALIVA GLAND OF TRIATOMA PALLIDIPENNIS
        ( C ) INDIVIDUAL ISOLATE: Ti 45

( i x ) FEATURE:
        ( A ) NAME/KEY: Protein
        ( B ) LOCATION: 19..160

( x i ) SEQUENCE DESCRIPTION: SEQ ID NO: 7:

```
Met  Lys  Thr  Ile  Ile  Ala  Val  Thr  Ile  Phe  Gly  Ile  Leu  Thr  Cys  Ala
               -15                      -10                      -5

Tyr  Ala  Ala  Glu  Gly  Asp  Asp  Cys  Ser  Ile  Glu  Lys  Ala  Met  Gly  Asp
          1                   5                        10

Phe  Lys  Pro  Glu  Glu  Phe  Phe  Asn  Gly  Thr  Trp  Tyr  Leu  Ala  His  Gly
15                       20                       25                       30

Pro  Asp  Val  Thr  Ser  Pro  Ala  Val  Cys  Gln  Lys  Phe  Thr  Thr  Ser  Gly
               35                       40                            45

Ser  Lys  Gly  Phe  Thr  Gln  Ile  Val  Glu  Ile  Gly  Tyr  Asn  Lys  Phe  Glu
               50                       55                       60

Ser  Asn  Val  Lys  Phe  Gln  Cys  Asn  Gln  Ala  Asp  Lys  Lys  Asn  Asp  Glu
          65                       70                       75

Gln  Tyr  Ser  Phe  Lys  Cys  Lys  Gly  Ser  Asp  Asn  Thr  Glu  Phe  Glu  Ala
     80                       85                       90

Asp  Phe  Thr  Phe  Ile  Ser  Val  Ser  Tyr  Asp  Asn  Phe  Ala  Leu  Val  Cys
95                       100                      105                      110

Arg  Ser  Ile  Thr  Phe  Thr  Ser  Gln  Pro  Lys  Glu  Asp  Asp  Tyr  Leu  Val
                    115                      120                      125

Phe  Glu  Arg  Thr  Lys  Ser  Asp  Thr  Asp  Pro  Asp  Ala  Asn  Glu  Ile  Cys
               130                      135                      140
```

( 2 ) INFORMATION FOR SEQ ID NO: 8:

( i ) SEQUENCE CHARACTERISTICS:
        ( A ) LENGTH: 160 amino acids
        ( B ) TYPE: amino acid sequence
        ( C ) STRANDEDNESS: single
        ( D ) TOPOLOGY: linear ( i i ) MOLECULE TYPE: protein ( v i ) ORIGINAL SOURCE:
        ( A ) ORGANISM: SALIVA GLAND OF TRIATOMA PALLIDIPENNIS
        ( C ) INDIVIDUAL ISOLATE: Ti 5

( i x ) FEATURE:
        ( A ) NAME/KEY: Protein (B) LOCATION: 19..160

(xi) SEQUENCE DESCRIPTION: SEQ ID NO: 8:

| Met | Lys | Thr | Ile -15 | Ile | Ala | Val | Thr | Ile -10 | Phe | Gly | Ile | Leu | Thr -5 | Cys | Ala |
| Tyr | Ala | Ala 1 | Glu | Gly | Asp | Asp 5 | Cys | Ser | Ile | Glu | Lys 10 | Ala | Met | Gly | Asp |
| Phe 15 | Lys | Pro | Glu | Glu | Phe 20 | Phe | Asn | Gly | Thr | Trp 25 | Tyr | Leu | Ala | His | Gly 30 |
| Pro | Gly | Val | Thr | Ser 35 | Pro | Ala | Val | Cys | Gln 40 | Lys | Phe | Thr | Thr | Ser 45 | Gly |
| Ser | Lys | Gly | Phe 50 | Thr | Gln | Ile | Val | Glu 55 | Ile | Gly | Tyr | Asn | Lys 60 | Phe | Glu |
| Ser | Asn | Val 65 | Lys | Phe | Gln | Cys | Asn 70 | Gln | Val | Asp | Asn | Lys 75 | Asn | Gly | Glu |
| Gln | Tyr 80 | Ser | Phe | Lys | Cys | Lys 85 | Ser | Ser | Asp | Asn | Thr 90 | Glu | Phe | Glu | Ala |
| Asp 95 | Phe | Thr | Phe | Ile | Ser 100 | Val | Ser | Tyr | Asp | Asn 105 | Phe | Ala | Leu | Val | Cys 110 |
| Arg | Ser | Ile | Thr | Phe 115 | Thr | Ser | Gln | Pro | Lys 120 | Glu | Asp | Asp | Tyr | Leu 125 | Val |
| Leu | Glu | Arg | Thr 130 | Lys | Ser | Asp | Thr | Asp 135 | Pro | Asp | Ala | Lys | Glu 140 | Ile | Cys |

(2) INFORMATION FOR SEQ ID NO: 9:

(i) SEQUENCE CHARACTERISTICS:
        (A) LENGTH: 429 nucleotides
        (B) TYPE: nucleotide sequence
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: SALIVA GLAND OF TRIATOMA PALLIDIPENNIS
        (C) INDIVIDUAL ISOLATE: Ti 12

(xi) SEQUENCE DESCRIPTION: SEQ ID NO: 9:

| | | | | | |
|---|---|---|---|---|---|
| GCAGAAGGTG | ACGACTGTTC | ATTAGAAAAA | GCTATGGGGG | ACTTTAAACC | AGAGGAGTTT | 60 |
| TTCAATGGAA | CGTGGTATTT | GGCTCATGGA | CCGGGCGTAA | CAAGTCCAGC | TGTCTGTCAG | 120 |
| AAATTTACTA | CTAGTGGAAG | CAAAGGTTTC | ACCCAAATTG | TTGAAATAGG | GTACAACAAA | 180 |
| TTTGAAAGTA | ACGTGAAATT | CCAATGCAAT | CAAGTTGATA | ATAAAATGA | CGAACAATAT | 240 |
| TCTTTCAAAT | GCAAAGGTAG | TGATAATACT | GAATTCGAAG | CAGATTTTAC | ATTTATTAGT | 300 |
| GTAAGCTATG | ATAACTTTGC | TTTAGTTTGT | AGAAGTATCA | TATTTACATC | ACAGCCTAAG | 360 |
| GAAGATGATT | ATTTGGTATT | CGAACGGACT | AAAAGTGACA | CAGATCCTGA | TGCTAATGAA | 420 |
| ATTTGTTAG | | | | | | 429 |

(2) INFORMATION FOR SEQ ID NO: 10:

(i) SEQUENCE CHARACTERISTICS:
        (A) LENGTH: 429 nucleotides
        (B) TYPE: nucleotide sequence
        (C) STRANDEDNESS: single
        (D) TOPOLOGY: linear (i i) MOLECULE TYPE: cDNA (i i i) HYPOTHETICAL: NO (i v) ANTI-SENSE: NO (v i) ORIGINAL SOURCE:
    (A) ORGANISM: SALIVA GLAND OF TRIATOMA PALLIDIPENNIS
    (C) INDIVIDUAL ISOLATE: Ti 28

(x i) SEQUENCE DESCRIPTION: SEQ ID NO: 10:

| | | | | | |
|---|---|---|---|---|---|
| GCAGAAGGTG | ACGACTGTTC | ATTAGAAAAA | GCTATGGGGG | ACTTTAAACC | AGAGGAGTTT | 60 |
| TTCAATGGAA | CGTGGTATTT | GGCTCATGGA | CCGGACGTAA | CAAGTCCAGC | TGTCTGTCAG | 120 |
| AAATTTACTA | CTAGTGGAAG | CAAAGGTTTC | ACCCAAATTG | TTGAAATAGG | GTACAACAAA | 180 |
| TTTGAAAGTA | ACGTGAAATT | CCAATGCAAT | CAAGTTGATA | ATAAAAATGA | CGAACAATAT | 240 |
| TCTTTCAAAT | GCAAAGGTAG | TGATAATACT | GAATTCGAAG | CAGATTTTAC | ATTTATTAGT | 300 |
| GTAAGCTATG | ATAACTTTGC | TTTAGTTTGT | AGAAGTATCA | TATTTACATC | ACAGCCTAAG | 360 |
| GAAGATGATT | ATTTGGTATT | CGAACGGACT | AAAAGTGACA | CAGATCCTGA | TGCTAATGAA | 420 |
| ATTTGTTAG | | | | | | 429 |

(2) INFORMATION FOR SEQ ID NO: 11:

(i) SEQUENCE CHARACTERISTICS:
        (A) LENGTH: 429 nucleotides
        (B) TYPE: nucleotide sequence
        (C) STRANDEDNESS: single
        (D) TOPOLOGY: linear (i i) MOLECULE TYPE: cDNA (i i i) HYPOTHETICAL: NO (i v) ANTI-SENSE: NO (v i) ORIGINAL SOURCE:
    (A) ORGANISM: SALIVA GLAND OF TRIATOMA PALLIDIPENNIS
    (C) INDIVIDUAL ISOLATE: Ti 45

(x i) SEQUENCE DESCRIPTION: SEQ ID NO: 11:

| | | | | | |
|---|---|---|---|---|---|
| GCAGAAGGTG | ATGACTGTTC | ATTAGAAAAA | GCTATGGGGG | ACTTTAAACC | AGAGGAGTTT | 60 |
| TTCAATGGAA | CGTGGTATTT | GGCTCATGGA | CCGGACGTAA | CAAGTCCAGC | TGTCTGTCAG | 120 |
| AAATTTACTA | CTAGTGGAAG | CAAAGGTTTC | ACCCAAATTG | TTGAAATAGG | GTACAACAAA | 180 |
| TTTGAAAGTA | ACGTGAAATT | CCAATGCAAT | CAAGCTGACA | AAAAAAATGA | CGAACAATAT | 240 |
| TCTTTCAAAT | GCAAAGGTAG | TGATAATACT | GAATTCGAAG | CAGATTTTAC | ATTTATTAGT | 300 |
| GTAAGCTATG | ATAACTTTGC | TCTAGTTTGT | AGAAGTATCA | CATTTACATC | ACAGCCTAAG | 360 |
| GAAGATGATT | ATTTGGTATT | CGAACGGACT | AAAAGTGACA | CAGATCCTGA | TGCTAATGAA | 420 |
| ATTTGTTAG | | | | | | 429 |

(2) INFORMATION FOR SEQ ID NO: 12:

(i) SEQUENCE CHARACTERISTICS:
        (A) LENGTH: 429 nucleotides
        (B) TYPE: nucleotide sequence
        (C) STRANDEDNESS: single
        (D) TOPOLOGY: linear (i i) MOLECULE TYPE: cDNA (i i i) HYPOTHETICAL: NO (i v) ANTI-SENSE: NO (vi) ORIGINAL SOURCE:
(A) ORGANISM: SALIVA GLAND OF TRIATOMA PALLIDIPENNIS
(C) INDIVIDUAL ISOLATE: Ti 5

(xi) SEQUENCE DESCRIPTION: SEQ ID NO: 12:

| | | | | | | |
|---|---|---|---|---|---|---|
| GCAGAAGGTG | ATGACTGTTC | AATAGAAAAA | GCTATGGGGG | ACTTTAAACC | AGAGGAGTTT | 60 |
| TTCAATGGAA | CGTGGTATTT | GGCTCATGGA | CCGGGCGTAA | CAAGTCCAGC | TGTCTGTCAG | 120 |
| AAATTTACTA | CTAGTGGAAG | CAAAGGTTTC | ACCCAAATTG | TTGAAATAGG | GTACAACAAA | 180 |
| TTTGAAAGTA | ACGTGAAATT | CCAATGCAAT | CAAGTTGACA | ATAAAAATGG | CGAACAATAT | 240 |
| TCTTTCAAAT | GCAAAAGTAG | TGATAATACT | GAATTCGAAG | CAGATTTTAC | ATTTATTAGT | 300 |
| GTAAGCTATG | ATAACTTTGC | TCTAGTTTGT | AGAAGTATCA | CATTTACATC | ACAGCCTAAG | 360 |
| GAAGATGATT | ATTTGGTATT | AGAACGGACT | AAAAGTGACA | CAGATCCTGA | TGCTAAAGAA | 420 |
| ATTTGTTAG | | | | | | 429 |

(2) INFORMATION FOR SEQ ID NO: 13:

(i) SEQUENCE CHARACTERISTICS:
(A) LENGTH: 483 nucleotides
(B) TYPE: nucleotide sequence
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: SALIVA GLAND OF TRIATOMA PALLIDIPENNIS
(C) INDIVIDUAL ISOLATE: Ti 12

(xi) SEQUENCE DESCRIPTION: SEQ ID NO: 13:

| | | | | | | |
|---|---|---|---|---|---|---|
| ATGAAGACGA | TCATTGCAGT | GACAATTTTT | GGAATTTTGA | CATGTGCATA | TGCAGCAGAA | 60 |
| GGTGACGAC | TGTTCATTAGA | AAAAGCTATG | GGGGACTTTA | AACCAGAGGA | GTTTTCAAT | 120 |
| GGAACGTGG | TATTTGGCTCA | TGGACCGGGC | GTAACAAGTC | CAGCTGTCTG | TCAGAAATTT | 180 |
| ACTACTAGT | GGAAGCAAAGG | TTTCACCCAA | ATTGTTGAAA | TAGGGTACAA | CAAATTTGAA | 240 |
| AGTAACGTG | AAATTCCAATG | CAATCAAGTT | GATAATAAAA | ATGACGAACA | ATATTCTTTC | 300 |
| AAATGCAAA | GGTAGTGATAA | TACTGAATTC | GAAGCAGATT | TTACATTTAT | TAGTGTAAGC | 360 |
| TATGATAAC | TTTGCTTTAGT | TTGTAGAAGT | ATCATATTTA | CATCACAGCC | TAAGGAAGAT | 420 |
| GATTATTTG | GTATTCGAACG | GACTAAAAGT | GACACAGATC | CTGATGCTAA | TGAAATTTGT | 480 |
| TAG | | | | | | 483 |

(2) INFORMATION FOR SEQ ID NO: 14:

(i) SEQUENCE CHARACTERISTICS:
(A) LENGTH: 483 nucleotides
(B) TYPE: nucleotide sequence
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: SALIVA GLAND OF TRIATOMA PALLIDIPENNIS
(C) INDIVIDUAL ISOLATE: Ti 28

( x i ) SEQUENCE DESCRIPTION: SEQ ID NO: 14:

| | | | | | |
|---|---|---|---|---|---|
| ATGAAGACGA | TCATTGCAGT | GACAATTTTT | GGAATTTTGA | CATGTGCATA | TGCAGCAGAA | 60
| GGTGACGACT | GTTCATTAGA | AAAAGCTATG | GGGGACTTTA | AACCAGAGGA | GTTTTTCAAT | 120
| GGAACGTGGT | ATTTGGCTCA | TGGACCGGAC | GTAACAAGTC | CAGCTGTCTG | TCAGAAATTT | 180
| ACTACTAGTG | GAAGCAAAGG | TTTCACCCAA | ATTGTTGAAA | TAGGGTACAA | CAAATTTGAA | 240
| AGTAACGTGA | AATTCCAATG | CAATCAAGTT | GATAATAAAA | ATGACGAACA | ATATTCTTTC | 300
| AAATGCAAAG | GTAGTGATAA | TACTGAATTC | GAAGCAGATT | TTACATTTAT | TAGTGTAAGC | 360
| TATGATAACT | TTGCTTTAGT | TTGTAGAAGT | ATCATATTTA | CATCACAGCC | TAAGGAAGAT | 420
| GATTATTTGG | TATTCGAACG | GACTAAAAGT | GACACAGATC | CTGATGCTAA | TGAAATTTGT | 480
| TAG | | | | | | 483

( 2 ) INFORMATION FOR SEQ ID NO: 15:

( i ) SEQUENCE CHARACTERISTICS:
        ( A ) LENGTH: 483 nucleotides
        ( B ) TYPE: nucleotide sequence
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: SALIVA GLAND OF TRIATOMA PALLIDIPENNIS
        ( C ) INDIVIDUAL ISOLATE: Ti 45

( x i ) SEQUENCE DESCRIPTION: SEQ ID NO: 15:

| | | | | | |
|---|---|---|---|---|---|
| ATGAAGACGA | TCATTGCAGT | GACAATTTTT | GGAATTTTGA | CATGTGCATA | TGCAGCAGAA | 60
| GGTGATGACT | GTTCATTAGA | AAAAGCTATG | GGGGACTTTA | AACCAGAGGA | GTTTTTCAAT | 120
| GGAACGTGGT | ATTTGGCTCA | TGGACCGGAC | GTAACAAGTC | CAGCTGTCTG | TCAGAAATTT | 180
| ACTACTAGTG | GAAGCAAAGG | TTTCACCCAA | ATTGTTGAAA | TAGGGTACAA | CAAATTTGAA | 240
| AGTAACGTGA | AATTCCAATG | CAATCAAGCT | GACAAAAAAA | ATGACGAACA | ATATTCTTTC | 300
| AAATGCAAAG | GTAGTGATAA | TACTGAATTC | GAAGCAGATT | TTACATTTAT | TAGTGTAAGC | 360
| TATGATAACT | TTGCTCTAGT | TTGTAGAAGT | ATCACATTTA | CATCACAGCC | TAAGGAAGAT | 420
| GATTATTTGG | TATTCGAACG | GACTAAAAGT | GACACAGATC | CTGATGCTAA | TGAAATTTGT | 480
| TAG | | | | | | 483

( 2 ) INFORMATION FOR SEQ ID NO: 16:

( i ) SEQUENCE CHARACTERISTICS:
        ( A ) LENGTH: 483 nucleotides
        ( B ) TYPE: nucleotide sequence
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: SALIVA GLAND OF TRIATOMA PALLIDIPENNIS
        ( C ) INDIVIDUAL ISOLATE: Ti 5

( x i ) SEQUENCE DESCRIPTION: SEQ ID NO: 16:

| ATGAAGACGA | TCATTGCAGT | GACAATTTTT | GGAATTTTGA | CATGTGCATA | TGCAGCAGAA | 60 |
|---|---|---|---|---|---|---|
| GGTGATGACT | GTTCAATAGA | AAAAGCTATG | GGGGACTTTA | AACCAGAGGA | GTTTTTCAAT | 120 |
| GGAACGTGGT | ATTTGGCTCA | TGGACCGGGC | GTAACAAGTC | CAGCTGTCTG | TCAGAAATTT | 180 |
| ACTACTAGTG | GAAGCAAAGG | TTTCACCCAA | ATTGTTGAAA | TAGGGTACAA | CAAATTTGAA | 240 |
| AGTAACGTGA | AATTCCAATG | CAATCAAGTT | GACAATAAAA | ATGGCGAACA | ATATTCTTTC | 300 |
| AAATGCAAAA | GTAGTGATAA | TACTGAATTC | GAAGCAGATT | TTACATTTAT | TAGTGTAAGC | 360 |
| TATGATAACT | TTGCTCTAGT | TTGTAGAAGT | ATCACATTTA | CATCACAGCC | TAAGGAAGAT | 420 |
| GATTATTTGG | TATTAGAACG | GACTAAAAGT | GACACAGATC | CTGATGCTAA | AGAAATTTGT | 480 |
| TAG | | | | | | 483 |

(2) INFORMATION FOR SEQ ID NO: 17:

(i) SEQUENCE CHARACTERISTICS:
       (A) LENGTH: 15 amino acids
       (B) TYPE: amino acid sequence
       (C) STRANDEDNESS: single
       (D) TOPOLOGY: linear (ii) MOLECULE TYPE: peptide (v) FRAGMENT TYPE: N-terminal (vi) ORIGINAL SOURCE:
       (A) ORGANISM: SALIVA GLAND OF TRIATOMA PALLIDIPENNIS (xi) SEQUENCE DESCRIPTION: SEQ ID NO: 17:

Ala Glu Gly Asp Asp Cys Ser Leu Glu Lys Ala Met Gly Asp Phe
   1               5                   10                  15

(2) INFORMATION FOR SEQ ID NO: 18:

(i) SEQUENCE CHARACTERISTICS:
       (A) LENGTH: 21 amino acids
       (B) TYPE: amino acid sequence
       (C) STRANDEDNESS: single
       (D) TOPOLOGY: linear (ii) MOLECULE TYPE: peptide (v) FRAGMENT TYPE: N-terminal (vi) ORIGINAL SOURCE:
       (A) ORGANISM: SALIVA GLAND OF TRIATOMA PALLIDIPENNIS (xi) SEQUENCE DESCRIPTION: SEQ ID NO: 18:

Ala Glu Gly Asp Asp Cys Ser Leu Glu Lys Ala Met Gly Asp Phe Xaa
   1               5                   10                  15

Pro Glu Glu Phe Phe
                20

(2) INFORMATION FOR SEQ ID NO: 19:

(i) SEQUENCE CHARACTERISTICS:
       (A) LENGTH: 21 amino acids
       (B) TYPE: amino acid sequence
       (C) STRANDEDNESS: single
       (D) TOPOLOGY: linear (ii) MOLECULE TYPE: peptide (v) FRAGMENT TYPE: N-terminal (vi) ORIGINAL SOURCE:
       (A) ORGANISM: SALIVA GLAND OF TRIATOMA PALLIDIPENNIS (xi) SEQUENCE DESCRIPTION: SEQ ID NO: 19:

```
Ala  Glu  Gly  Asp  Asp  Cys  Ser  Leu  Glu  Lys  Ala  Met  Gly  Asp  Phe  Lys
1                   5                        10                       15

Pro  Glu  Glu  Phe  Phe
                20
```

( 2 ) INFORMATION FOR SEQ ID NO: 20:

( i ) SEQUENCE CHARACTERISTICS:
        ( A ) LENGTH: 18 amino acids
        ( B ) TYPE: amino acid sequence
        ( C ) STRANDEDNESS: single
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: SALIVA GLAND OF TRIATOMA PALLIDIPENNIS ( x i ) SEQUENCE DESCRIPTION: SEQ ID NO: 20:

```
Ala  Met  Gly  Asp  Phe  Lys  Pro  Glu  Glu  Phe  Phe  Xaa  Gly  Thr  Arg  Tyr
1                   5                        10                       15

Leu  Ala
```

( 2 ) INFORMATION FOR SEQ ID NO: 21:

( i ) SEQUENCE CHARACTERISTICS:
        ( A ) LENGTH: 12 amino acids
        ( B ) TYPE: amino acid sequence
        ( C ) STRANDEDNESS: single
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: SALIVA GLAND OF TRIATOMA PALLIDIPENNIS ( x i ) SEQUENCE DESCRIPTION: SEQ ID NO: 21:

```
Gly  Phe  Thr  Gln  Ile  Val  Glu  Ile  Gly  Tyr  Asn  Lys
1                   5                        10
```

( 2 ) INFORMATION FOR SEQ ID NO: 22:

( i ) SEQUENCE CHARACTERISTICS:
        ( A ) LENGTH: 8 amino acids
        ( B ) TYPE: amino acid sequence
        ( C ) STRANDEDNESS: single
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: SALIVA GLAND OF TRIATOMA PALLIDIPENNIS ( x i ) SEQUENCE DESCRIPTION: SEQ ID NO: 22:

```
Asn  Gly  Glu  Gln  Tyr  Ser  Phe  Lys
1                   5
```

( 2 ) INFORMATION FOR SEQ ID NO: 23:

( i ) SEQUENCE CHARACTERISTICS:
        ( A ) LENGTH: 44 nucleotides
        ( B ) TYPE: nucleotide sequence
        ( C ) STRANDEDNESS: single
        ( D ) TOPOLOGY: linear ( i i ) MOLECULE TYPE: other nucleic acid
( A ) DESCRIPTION: /desc = "sense primer"

( i i i ) HYPOTHETICAL: NO ( i v ) ANTI-SENSE: NO ( i x ) FEATURE:
( A ) NAME/KEY: modified_base
( B ) LOCATION: one-of(3, 9, 21, 24, 33, 39)
( D ) OTHER INFORMATION: /mod_base=i ( x i ) SEQUENCE DESCRIPTION: SEQ ID NO: 23:

GCNGARGGNG AYGAYTGYTC NCTNGARAAR GCNATGGGNG AYTT 44

( 2 ) INFORMATION FOR SEQ ID NO: 24:

( i ) SEQUENCE CHARACTERISTICS:
( A ) LENGTH: 32 nucleotides
( B ) TYPE: nucleotide sequence
( C ) STRANDEDNESS: single
( D ) TOPOLOGY: linear ( i i ) MOLECULE TYPE: other nucleic acid
( A ) DESCRIPTION: /desc = "antisense primer"

( v i ) ORIGINAL SOURCE:
( A ) ORGANISM: SALIVA GLAND OF TRIATOMA PALLIDIPENNIS ( i i i ) HYPOTHETICAL: NO ( i v ) ANTI-SENSE: YES ( i x ) FEATURE:
( A ) NAME/KEY: modified_base
( B ) LOCATION: one-of(9, 19, 27)
( D ) OTHER INFORMATION: /mod_base=i ( x i ) SEQUENCE DESCRIPTION: SEQ ID NO: 24:

TTRTTRTANC CRATYTCNA CRATYTGNGTR AA 32

( 2 ) INFORMATION FOR SEQ ID NO: 25:

( i ) SEQUENCE CHARACTERISTICS:
( A ) LENGTH: 7 amino acids
( B ) TYPE: amino acid sequence
( C ) STRANDEDNESS: single
( D ) TOPOLOGY: linear ( i i ) MOLECULE TYPE: peptide ( v ) FRAGMENT TYPE: C-terminal ( i x ) FEATURE:
( A ) NAME/KEY: Region
( B ) LOCATION: 1..7
( D ) OTHER INFORMATION: /note= "C-terminal end of modified
cyclophilin a"

( x i ) SEQUENCE DESCRIPTION: SEQ ID NO: 25:

Phe Ser Ala Ser Ala Leu Ala
1               5

( 2 ) INFORMATION FOR SEQ ID NO: 26:

( i ) SEQUENCE CHARACTERISTICS:
( A ) LENGTH: 57 nucleotides
( B ) TYPE: nucleotide sequence
( C ) STRANDEDNESS: single
( D ) TOPOLOGY: linear ( i i ) MOLECULE TYPE: other nucleic acid
( A ) DESCRIPTION: /desc = "sense primer"

( i i i ) HYPOTHETICAL: NO ( i v ) ANTI-SENSE: NO ( i x ) FEATURE:
    ( A ) NAME/KEY: Region
    ( B ) LOCATION: 1..57
    ( D ) OTHER INFORMATION: /note= "derived from an amino acid sequence of modified cyclophilin a"

( x i ) SEQUENCE DESCRIPTION: SEQ ID NO: 26:

GCGATAACAT GTTCAAAAGC ACCCTGGCGG CGATGGCTGC TGTTTTCGCT CTGTCTG     57

( 2 ) INFORMATION FOR SEQ ID NO: 27:

( i ) SEQUENCE CHARACTERISTICS:
    ( A ) LENGTH: 58 nucleotides
    ( B ) TYPE: nucleotide sequence
    ( C ) STRANDEDNESS: single
    ( D ) TOPOLOGY: linear ( i i ) MOLECULE TYPE: other nucleic acid
    ( A ) DESCRIPTION: /desc = "antisense primer"

( i i i ) HYPOTHETICAL: NO ( i v ) ANTI-SENSE: YES ( i x ) FEATURE:
    ( A ) NAME/KEY: Region
    ( B ) LOCATION: 1..58
    ( D ) OTHER INFORMATION: /note= "derived from an amino acid sequence of modified cyclophilin a"

( x i ) SEQUENCE DESCRIPTION: SEQ ID NO: 27:

CGCTATAAGC TTCTGCAGGC TAGCGCGCTC GCGCTGAAAG CAGACACAGT CGAAACAG     58

( 2 ) INFORMATION FOR SEQ ID NO: 28:

( i ) SEQUENCE CHARACTERISTICS:
    ( A ) LENGTH: 28 nucleotides
    ( B ) TYPE: nucleotide sequence
    ( C ) STRANDEDNESS: single
    ( D ) TOPOLOGY: linear ( i i ) MOLECULE TYPE: other nucleic acid
    ( A ) DESCRIPTION: /desc = "sense primer"

( i i i ) HYPOTHETICAL: NO ( i v ) ANTI-SENSE: NO ( v i ) ORIGINAL SOURCE:
    ( A ) ORGANISM: SALIVA GLAND OF TRIATOMA PALLIDIPENNIS ( i x ) FEATURE:
    ( A ) NAME/KEY: Region
    ( B ) LOCATION: 1..28
    ( D ) OTHER INFORMATION: /note= "derived from an amino acid sequence of thrombin inhibitor"

( x i ) SEQUENCE DESCRIPTION: SEQ ID NO: 28:

GCGATAGCTA GCAGCAGAAG GTGACGAC     28

( 2 ) INFORMATION FOR SEQ ID NO: 29:

( i ) SEQUENCE CHARACTERISTICS:
    ( A ) LENGTH: 43 nucleotides
    ( B ) TYPE: nucleotide sequence
    ( C ) STRANDEDNESS: single
    ( D ) TOPOLOGY: linear ( i i ) MOLECULE TYPE: other nucleic acid (A) DESCRIPTION: /desc = "antisense primer"

(iii) HYPOTHETICAL: NO (iv) ANTI-SENSE: YES (vi) ORIGINAL SOURCE:
    (A) ORGANISM: SALIVA GLAND OF TRIATOMA PALLIDIPENNIS (ix) FEATURE:
    (A) NAME/KEY: Region
    (B) LOCATION: 1..43
    (D) OTHER INFORMATION: /note= "derived from an amino acid sequence of thrombin inhibitor"

(xi) SEQUENCE DESCRIPTION: SEQ ID NO: 29:

```
GCGATAGGAT   CCAAGCTTAC   TAACAAATTT   CATTAGCATC   AGG            43
```

THROMBIN INHIBITOR FROM THE SALIVA OF PROTOSTOMIA

This application is a continuation of application Ser. No. 08/460,383, filed Jun. 2, 1995, now abandoned.

The invention relates to proteins, which are thrombin inhibitors from the saliva of protostomia.

PRIOR ART

Thrombin has a key function in the thrombus formation in blood vessels. It catalyzes the cleavage of fibrinogen to fibrin. It leads to the formation of blood clots. Further, it induces the aggregation of blood platelets. The enzyme is involved in the pathogenesis of different diseases, such as, e.g., arterial and venous thrombosis or arteriosclerosis.

Therefore, the use of a thrombin inhibitor for treatment of thromboses is promising. The most important previously known thrombin inhibitors are antithrombin III-heparin and hirudin. Antithrombin III is a protein occurring in plasma with a molecular weight of 58 kDa. Antithrombin III binds first to heparin, which is a polysaccharide. Then, the antithrombin III-heparin complex binds to thrombin and inhibits this thrombin. A very stable complex of thrombin and antithrombin III results and antithrombin III is cleaved from thrombin. In addition to thrombin, antithrombin III also inhibits other serine proteases such as, e.g., factor Xa (Pratt, C. W. and Church, F. C. (1991) "Antithrombin: Structure and Function," Seminars in Hematology 28: 3–9).

The protein hirudin was isolated from the *Hirudo medicinalis* leech. It has a molecular weight of about 7 kDa and binds to thrombin by ionic interaction. It is specific for thrombin (Johnson, P. H. et al. (1989) "Biochemistry and Genetic engineering of hirudin," Seminars in Thrombosis and Hemostasis 15: 302–315).

DESCRIPTION OF THE INVENTION

In addition to the previously mentioned thrombin inhibitors, which are included in the prior art, other inhibitors are necessary which have another mechanism of action or an increased activity.

The invention provides natural proteins or proteins that can be synthetically produced, which are thrombin inhibitors and can be isolated from the saliva of insects which suck the blood of mammals.

Proteins according to the invention which can be isolated from the *Triatoma pallidipennis* cone-nosed bug are preferred.

The proteins according to the invention can be of natural origin. The proteins are obtained by the saliva being purified. Also, it is possible to isolate the proteins from the salivary glands or to take the cells synthesizing the protein from the salivary glands and to keep them in the culture. The supernatants produced by this cell culture are harvested and worked up. The cell supernatant is purified and the proteins according to the invention are isolated and enriched. All enrichment stages of the isolation and the purification are part of the invention. Preferred are the enrichment stages of the isolation and purification in which the proteins according to the invention can be used for pharmaceutical purposes. Thus, purifications of 50% of the thrombin inhibitor are achieved relative to the total protein, preferred are 85%, more preferred 95% and most preferred 99% of the thrombin inhibitor relative to the total protein.

The invention comprises not only the proteins which can be isolated from *Triatoma pallidipennis*, but also proteins which can be synthesized from other types of insects. Thus, in addition to the proteins which can be isolated from *Triatoma pallidipennis* and which are in the group of the most preferred, other proteins are preferred which are derived from *Triatoma infestans, Triatoma dimidiata, Triatoma maculata, Rhodnius prolixus, Panstrongylus megistus* and *Panstrongylus infestans*.

It is likewise possible to produce the proteins according to the invention synthetically. Included in this is the protein synthesis according to J. M. SEWART and J. D. YOUNG, San Francisco, 1969 and J. MEIENHOFER, Hormonal Proteins and Peptides, Vol. 2, p. 46, Academic Press (New York), 1973 and E. SCHODER and K. LUBKE, The Peptides, Vol. 1, Academic Press (New York), 1965. The recombinant proteins, which are produced according to known processes, are also included in the synthetically produced proteins. Depending on the host organism, the proteins according to the invention can be glycosylated or, if they are synthesized in prokaryotes, unglycosylated.

The function of the inhibitor is to be determined in different testing systems. Standard testing processes are described in Examples 2 to 4 and 9.

The proteins according to the invention can be detected in the saliva of insects which suck the blood of mammals. These proteins are usually synthesized from cells of the salivary glands. Therefore, the proteins can be isolated from the saliva. The proteins according to the invention are not limited to this production method and isolation. Rather, also comprised are all synthetically-produced thrombin inhibitors according to the invention which can be detected in the saliva and isolated from it.

N-TERMINAL SEQUENCES OF MATURE PROTEIN

The invention further comprises a natural protein or a protein that can be synthetically produced, which is a thrombin inhibitor and can be isolated from the saliva of insects which suck the blood of mammals, preferably of *Triatoma pallidipennis*, a) in which the protein, as active protein, has an N-terminal sequence (SEQ ID NO: 19) as follows:

Ala—Glu—Gly—Asp—Asp—Cys—Ser—Leu—Glu—Lys—
$\qquad\qquad\qquad\qquad\qquad$ 5 $\qquad\qquad\qquad\qquad$ 10

Ala—Met—Gly—Asp—Phe—Lys—Pro—Glu—Glu—Phe—Phe ...
$\qquad\qquad\qquad\qquad\qquad$ 15 $\qquad\qquad\qquad\qquad$ 20 or b) in which the protein, as active protein, exhibits allelic modifications of the N-terminal amino acid sequence previously mentioned under a), in which one or two amino acids of the N-terminal amino acid sequence are substituted, deleted or inserted, without in this case the activity of the active protein being significantly affected, or c) in which the protein, as active protein, exhibits post-translational modifications of the N-terminal sequences under a) and b), which do not significantly affect the activity of the active protein.

SEQUENCES OF MATURE PROTEINS

The invention further comprises a protein which is a thrombin inhibitor and d) which, as active mature protein, has one of the following sequences:

i) SEQ ID NO:1
ii) SEQ ID NO:2
iii) SEQ ID NO:3
iv) SEQ ID NO:4 or e) which, as active mature protein, exhibits allelic modifications of one of the amino acid sequences previously mentioned under d), in which at least one amino acid of the amino acid sequence is substituted, deleted or inserted, without in this case the activity of the active protein being significantly affected, or f) which, as active mature protein, exhibits posttranslational modifications of one of the sequences under d) and e), which do not significantly affect the activity of the active protein.

All allelic modifications, which comprise the substitutions, the deletions and/or the insertions of up to 30 amino acids, are part of the group of proteins according to the invention. Preferred are deletions, substitutions and/or insertions of up to 20 amino acids, more preferred of up to 10 amino acids, most preferred are the deletions, substitutions and/or insertions of one, two, three, four, five, six, seven, eight or nine amino acids.

SEQUENCES OF MATURE PROTEINS WITH SIGNAL SEQUENCE

Another embodiment of the proteins according to the invention consists in a protein, which consists of a signal sequence and a mature protein according to the invention, g) in which the protein has one of the following sequences:
i) SEQ ID NO:5
ii) SEQ ID NO:6
iii) SEQ ID NO:7
iv) SEQ ID NO:8 or h) in which the protein exhibits allelic modifications of one of the amino acid sequences previously mentioned under g), in which at least one amino acid of the amino acid sequence is substituted, deleted or inserted, without in this case the activity of the mature active protein being significantly affected, or i) in which the protein exhibits posttranslational modifications of one of the sequences under g) and h) which do not significantly affect the activity of the active mature protein.

All allelic modifications, which comprise the substitutions, the deletions and/or the insertions of up to 32 amino acids, are part of the group of proteins according to the invention. Preferred are deletions, substitutions and/or insertions of up to 21 amino acids, more preferred of up to 11 amino acids, most preferred are the deletions, substitutions and/or insertions of one, two, three, four, five, six, seven, eight or nine amino acids.

Most preferred are proteins according to the invention which are recombinant proteins. In this case, the proteins can be glycosylated.

The proteins according to the invention comprise the mature proteins and the corresponding precursor proteins, which consist of a "signal sequence" and the sequence of the mature protein. In this case, the "signal sequence" precedes the sequence of the mature protein. The mature protein begins with the previously mentioned N-terminal sequence under point a). The "signal sequence" is necessary for the penetration of the endoplasmic reticulum.

cDNA OR DNA CODING FOR THE PROTEINS ACCORDING TO THE INVENTION

The invention further also comprises cDNA or DNA, which codes a mature thrombin inhibitor, aa) in which the cDNA or DNA codes one of the following amino acid sequences:
i) SEQ ID NO:1
ii) SEQ ID NO:2
iii) SEQ ID NO:3
iv) SEQ ID NO:4 or bb) in which the cDNA or DNA codes allelic modifications of one of the amino acid sequences under aa), in which at least one amino acid of the amino acid sequence is substituted, deleted or inserted, without in this case the activity of the active protein being significantly affected.

The allelic modifications were defined above under the point "Sequences of mature proteins."

The invention further comprises a cDNA or DNA, which codes a thrombin inhibitor, cc) in which the cDNA or DNA has one of the following nucleotide sequences:
i) SEQ ID NO:9
ii) SEQ ID NO:10
iii) SEQ ID NO:11
iv) SEQ ID NO:12 or dd) in which the cDNA or DNA exhibits an allelic modification of one of the nucleotide sequences under cc), in which at least one nucleotide is substituted, deleted or inserted, without in this case the activity of the protein, which is coded under cc) by the allelic modification of the nucleotide sequence, being significantly affected.

All DNA constructs also then are included in the listed sequences according to the invention, when those nucleotides are exchanged that code the same amino acid because of the degenerated code. The exchange of such nucleotides is obvious and the corresponding amino acids are disclosed in every biochemistry textbook. (R. KNIPPERS, 1982, 3rd Edition, Molekulare Genetik [Molecular Genetics], Georg Thieme Verlag)

All allelic modifications, which result in a change of the amino acid sequence, are part of the invention, if these modifications comprise the substitutions, the deletions and/or the insertions of up to 30 amino acids. Preferred are deletions, substitutions and/or insertions of up to 20 amino acids, more preferred of up to 10 amino acids, most preferred are the deletions, substitutions and/or insertions of one, two, three, four, five, six, seven, eight or nine amino acids.

The invention also further comprises a genetic material, which also contains a signal sequence in addition to the sequence coding the mature protein. This signal sequence has been found in the cDNA bank, other signal sequences are also possible which allow an expression and secretion of protein.

Thus, the invention comprises a cDNA or DNA, which codes a thrombin inhibitor with signal sequence, ee) in which the cDNA or DNA has one of the following nucleotide sequences:
i) SEQ ID NO:13
ii) SEQ ID NO:14
iii) SEQ ID NO:15
iv) SEQ ID NO:16 or ff) in which the cDNA or DNA exhibits an allelic modification of one of the nucleotide sequences under ee), in which at least one nucleotide is substituted, deleted or inserted, without in this case the activity of the mature protein, which including its signal sequence is coded by the allelic modifications of the nucleotide sequence under ee), being significantly affected.

The allelic modifications were previously defined under dd).

If the activity of the protein is provided to determine whether the allelic modification is included under the group of proteins according to the invention, the mature protein can always be measured, even if the signal sequence is also indicated. Should the signal sequence be provided, the function can always be measured on the protein, so that it is obtained after removal of the signal sequence.

Further, the invention comprises binding molecules (for example, peptides or their derivatives), single-chain proteins, antibodies or fragments of the antibodies, which recognize domains specific to the mature protein according to the invention. If the purified protein according to the invention is present, it is easily possible for one skilled in the art to produce monoclonal antibodies. In this case, the known method of Köhler and Milstein and its further developments are used. Thus, a mouse is immunized several times with the purified protein specifically by the conventional method, the splenocytes are removed and fused with suitable tumor cells. The hybrids are then selected.

The proteins of the invention can be isolated from the saliva of the *Triatoma pallidipennis* cone-nosed bug. The purification takes place by a gel filtration and a subsequent affinity chromatography on thrombin Sepharose (see Example 1). The proteins have the previously described amino acid sequences. They have a molecular weight of about 18,000±3,000 Da (see Example 6). The isoelectric point is in the range of pH 4.5 to 5.2, if the method described in Example 8 is used.

The proteins of the invention inhibit the action of thrombin in the blood clotting and in the activation of platelets and in the amidolytic test. The testing systems are described in Examples 2, 3, 4 and 9. The proteins inhibit the clotting in a concentration of 8 nmol/l at a thrombin concentration of 1.27 nmol/l. They inhibit the thrombin-induced platelet aggregation to 100% in a concentration of 15 ng/ml. This concentration corresponds in a used thrombin concentration of 0.06 IU/ml=0.812 pmol/ml (IU=international units) to a molar ratio of thrombin to the protein according to the invention of about 1:1. On the other hand, the proteins of the invention inhibit the activity of thrombin in the amidolytic test at a ratio of thrombin to the protein according to the invention of 1:87 only to about 50%. In a concentration of 35 nmol/l, the proteins of the invention lengthen the thrombin time (1 IU/ml) 5-fold.

The proteins of the invention are specific for thrombin. Other serine proteases (e.g., factor Xa or trypsin) are not demonstrably inhibited even in a 40-fold excess (see example 7).

VECTORS WITH THE DNA ACCORDING TO THE INVENTION

Another part of the invention is a vector, which contains a cDNA or DNA according to the invention, further a matching promoter and optionally a matching enhancer. Also, one more "signal sequence" can be comprised. Vectors are described in detail in European publications EP 0 480 651, EP 0 462 632 and EP 0 173 177.

Another embodiment of the invention consists in a eukaryotic or prokaryotic host cell, which is transformed with a vector according to the invention.

ALLELIC MODIFICATIONS

Most deletions, insertions and substitutions seem to have not resulted in any drastic change in the characteristic of the protein of the invention. Since it is difficult to indicate in advance the exact effect of a substitution, a deletion or an insertion, the function of the changed protein has to be compared with the function of the protein according to the invention. The methods to be used for this purpose are indicated, for example, in Examples 2 to 4 and 9. The protein according to Seq. Id. Nos. 1 to 4, also the protein which is purified according to Example 1 and also the purification method of Example 1 for the comparison protein are used as a standard.

The genetic code is degenerated, i.e., most amino acids of more than one codon are coded from three nucleotides. Therefore, several allelic modifications on the level of the nucleotides do not lead to a change of the amino acid sequence. Therefore, allelic modifications take place in particular on the level of the DNA and can have a secondary effect on the amino acid sequence.

The cDNA or DNA sequences, which code the proteins according to the invention, can be modified according to conventional techniques to produce variants of the proteins according to the invention, which have basically the same activity as the described and characterized proteins of the invention. In this connection, the activity is measured as it is described in Examples 2 to 4 and 9.

Amino acids can be substituted as represented in Table 1, without the function of the protein thus being significantly affected. In each individual case, it is to be decided by the activity test what influence the change has on the function of the protein.

TABLE 1

| USUAL SUBSTITUTION OF AMINO ACIDS IN A PROTEIN | |
|---|---|
| ORIGINAL AMINO ACID | SUBSTITUTION PERFORMED BY WAY OF EXAMPLE |
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

The functions or the immunological identity are significantly changed if substituents are selected which are less conservative in the substitution than the amino acids shown in Table 1. Such significant changes can be achieved by substitutions with amino acids, which differ more in their structure and in the functional groups. Significant changes have an effect that the three-dimensional structure is changed and/or that for example, the pleated sheet structure or the helical structure is affected. Also, interactions of the charges and the hydrophobic chains are to be observed in the changes.

The mutations are defined by the homology (similarity) of two proteins coming up for comparison. The term homology comprises similar amino acids (for example, Table 1) and gaps in the sequences of the amino acids (homology= similarity). The proteins according to the invention have amino acid sequences which have a homology of at least 80%, preferably 90%, more preferably 95% and most preferably 98% of the structure according to the invention, as they are defined by the sequences under d) or g) (Seq. Id. Nos. 1 to 8) and as they are further obtained after the purification according to Example 1.

As previously mentioned, the invention also comprises modifications of the DNA or cDNA. These modified sequences hybridize under stringent conditions with the DNA sequences, which code the proteins according to the invention (see sequences under aa); cc) and ee)). The cDNA or DNA sequences have nucleotide sequences, which have an identity including shorter (up to 15 nucleotides) deletions and insertions of at least 70%, preferably 82%, more preferably 90% and most preferably 95% with the cDNA or DNA sequences according to the invention (see aa), cc) and ee)). The identity including short (up to 15 nucleotides) deletions and insertions can be measured by a hybridization, as it is described in R. KNIPPERS, Molekulare Genetik (Molecular Genetics), 1982, Third Edition, Georg Thieme Verlag Stuttgart, New York.

POSTTRANSLATIONAL MODIFICATIONS

The previously mentioned posttranslational modifications are to be understood to mean changes which occur during or after the translation. This includes the glycosylation, the formation of disulfide bridges, the chemical modifications of the amino acids, thus, for example, the sulfation, which is described in connection with hirudin. (J. W. FENTON (1989) "Thrombin Interactions with Hirudin," Seminars in Thrombosis and Hemostasis 15: 265–268)

The glycosylation is a basic function of the endoplasmic reticulum and/or the Golgi apparatus. The sequence and the branching of the oligosaccharides are formed in the endoplasmic reticulum and changed in the Golgi apparatus. The oligosaccharides can be N-linked oligosaccharides (asparagine-linked) or O-linked oligosaccharides (serine-, threonine- or hydroxylysine-linked). The form of the glycosylation is dependent on the produced cell type and on the type from which the corresponding cell type is derived. The extent and the type of the glycosylation can be affected by substances, as it is described in European publication EP 0 222 313. The variation of the glycosylation can change the function of the protein.

Proteins often form covalent bonds inside the chains. These disulfide bridges are produced between two cysteines. In this connection, the protein is specifically pleated. The disulfide bridges stabilize the three-dimensional structure of the proteins.

Further, the amino acids can be changed, as it is described in international publication WO 91/10684. Also, the protein can be sulfated. This change is described in connection with hirudin.

ISOLATION AND PRODUCTION OF THE PROTEINS ACCORDING TO THE INVENTION

The invention further comprises a process for the production of proteins according to the invention with the following steps:
Cultivation of a host cell, which is transformed with a vector, which contains a cDNA or DNA according to the invention, and
isolation and purification of the protein or proteins.

The proteins are preferably purified according to Example 1. But other isolation and purification methods are also possible:
Methods of Enzymology, Volume 182: Guide to Protein Purification, ed. Murray P. DEUTSCHER, Academic Press, 1990;
Protein Purification Application—A Practical Approach, ed. E. L. V. HARRIS and S. ANGEL, IRL-Press 1990;
Protein Purification, Principles and Practice, Ropert SCOPES, Springer-Verlag 1982; and
Protein Purification, Principles, High Resolution Methods and Applications, ed. H.-C. JANSON and L. RYDEN, VCH publishers 1989.

The invention also comprises a process for the purification of proteins according to the invention, in which the proteins are isolated, purified on at least one column and then concentrated by evaporation. Preferred are chromatography columns or adsorption chromatography columns.

The invention comprises, moreover, a process for the purification of proteins according to the invention, in which the process consists of the following steps:
Applying the saliva on a "Superose 12 HR-column" and elution and
renewed application on a CH-activated Sepharose column, to which thrombin was previously coupled, and elution.

The purification is described in detail in Example 1.

USE AS PHARMACEUTICAL AGENT

The proteins according to the invention have pharmacological effects and can therefore be used as pharmaceutical active ingredients. The invention also comprises a pharmaceutical agent, which contains one of the proteins according to the invention or a mixture of them. Further, a pharmaceutical composition which contains one of the proteins according to the invention or a mixture of proteins according to the invention, in the presence of pharmaceutically compatible and acceptable compounds and vehicles, is part of the invention. The invention also comprises a pharmaceutical composition which contains one of the pharmaceutically active proteins according to the invention or their mixture, and a pharmaceutically compatible salt or a pharmaceutically compatible vehicle.

In particular, the proteins of sequence protocol nos. 1 to 4 according to the invention show an inhibition of thrombin activity.

The inhibition of thrombin activity can be detected in the clotting test (see Example 2), in the blood-platelet aggregation test (see Example 3) and in the amidolytic test (see Example 4) and by measuring the thrombin time (see Example 9). The measurement of the thrombin time is the preferred testing system.

The proteins according to the invention show a lengthening of the thrombin time at concentrations of 10 to 60 nmol/l (thrombin concentration 1 IU/ml). At a concentration of 58 nmol/l, a 9-fold lengthening takes place. Higher concentrations can be used without disturbing the testing system. Thus, the proteins according to the invention can be used in concentrations of 10 to 200 nmol/l.

The test results of this in vitro test show that the proteins according to the invention can be used as pharmaceutical agents or for medical treatment. These test results can be transferred from the in vitro testing system to an in vivo system, since an established test arrangement is involved in the clotting test (M. TALBOT (1989) "Biology of Recombinant Hirudin, A New Prospect in the Treatment of Thrombosis" Seminars in Thrombosis and Hemostasis 15: 293–301). The proteins of the invention can therefore be used for the treatment and prevention of thromboses, unstable angina or arteriosclerosis, or for prevention of a reblockage of vessels after PTCA/PTA (angioplasty with a balloon catheter) or for preventing the blood clotting in hemodialysis. The proteins of the invention can be used as an antithrombotic and/or antiarteriosclerotic medicine in mammals, especially humans, for treatment of thrombotic and/or arteriosclerotic symptoms. These can occur with tearing of arteriosclerotic aggregations (plaques), in the destruction of endothelial tissue, such as, for example, in sepsis, in transplants or in unstable angina. They can also be used to avoid renewed blockages after the treatment of myocardial infarctions and/or in fibrinolysis or angioplasty. In this case, the protein of the invention can be administered before, during and/or after the insertion of the catheter.

The invention further provides (i) the use of one of the proteins according to the invention or their mixture for the production of a medicine for the treatment of
thromboses, unstable angina or arteriosclerosis or for prevention of a reblockage of vessels after PTCA/PTA or for prevention of blood clotting in hemodialysis;

(ii) a process for the treatment of thromboses, unstable angina or arteriosclerosis, or for the prevention of a reblockage of vessels after PTCA/PTA or thrombolysis or for the prevention of blood clotting in hemodialysis, which process comprises an administration of an amount of protein according to the invention in which the amount suppresses the disease and in which the amount of protein is given to a patient who requires such a medicine;

(iii) a pharmaceutical composition for the treatment of thromboses, unstable angina or arteriosclerosis, or for the prevention of a reblockage of vessels after PTCA/PTA or thrombolysis or for the prevention of blood clotting in hemodialysis, which comprises treatment of one of the proteins according to the invention or their mixture and at least one pharmaceutically compatible vehicle and additive.

For this therapeutic action, different doses are suitable. They depend, for example, on the protein used, on the host, on the type of administration and on the type and severity of the conditions to be treated.

But in general, satisfactory results in animals are to be expected when the daily doses comprise a range of 2 $\mu$g to 2000 $\mu$g per kg of body weight. In larger mammals, for example, in humans, a recommended daily dose lies in the range of 2 to 2000 $\mu$g per kg of body weight when the protein purified according to Example 1 is used. For example, this dose is suitably administered in partial doses up to four times daily. The daily doses in the short-term treatment of acute clots with 20 to 2000 $\mu$g per kg of body weight can be greater than the doses in the chronic treatment with 2 to 200 $\mu$g per kg of body weight.

Satisfactory results are also to be expected when the protein of the invention is administered subcutaneously. Preferred is the specific injection in the part of the body in which clots have formed.

The proteins according to the invention can be administered in every usual method, especially in the form of injection solutions or suspensions.

This invention makes available pharmaceutical compositions which comprise one of the proteins according to the invention or their mixture and at least one pharmaceutically compatible vehicle or additive. Such compositions can be produced according to known processes. In this case, reference is to be made to Remington's Pharmaceutical Science, 15th ed., Mack Publishing Company, East Pennsylvania (1980).

Figure 2:
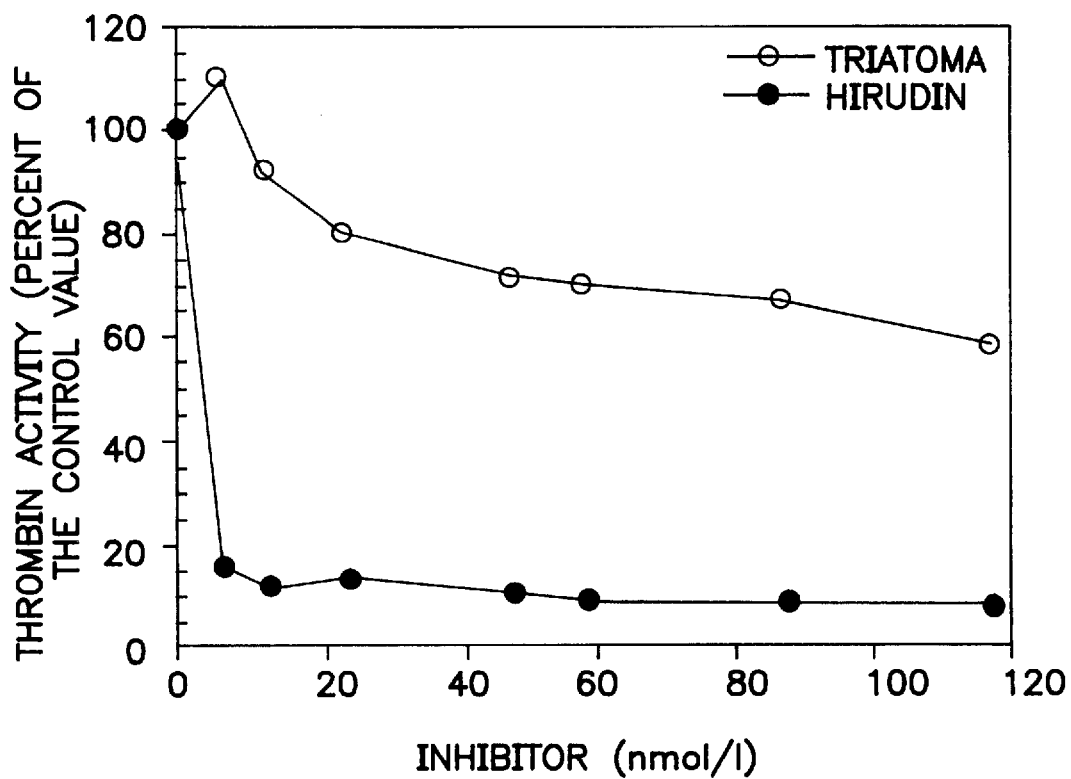
Figure 3:
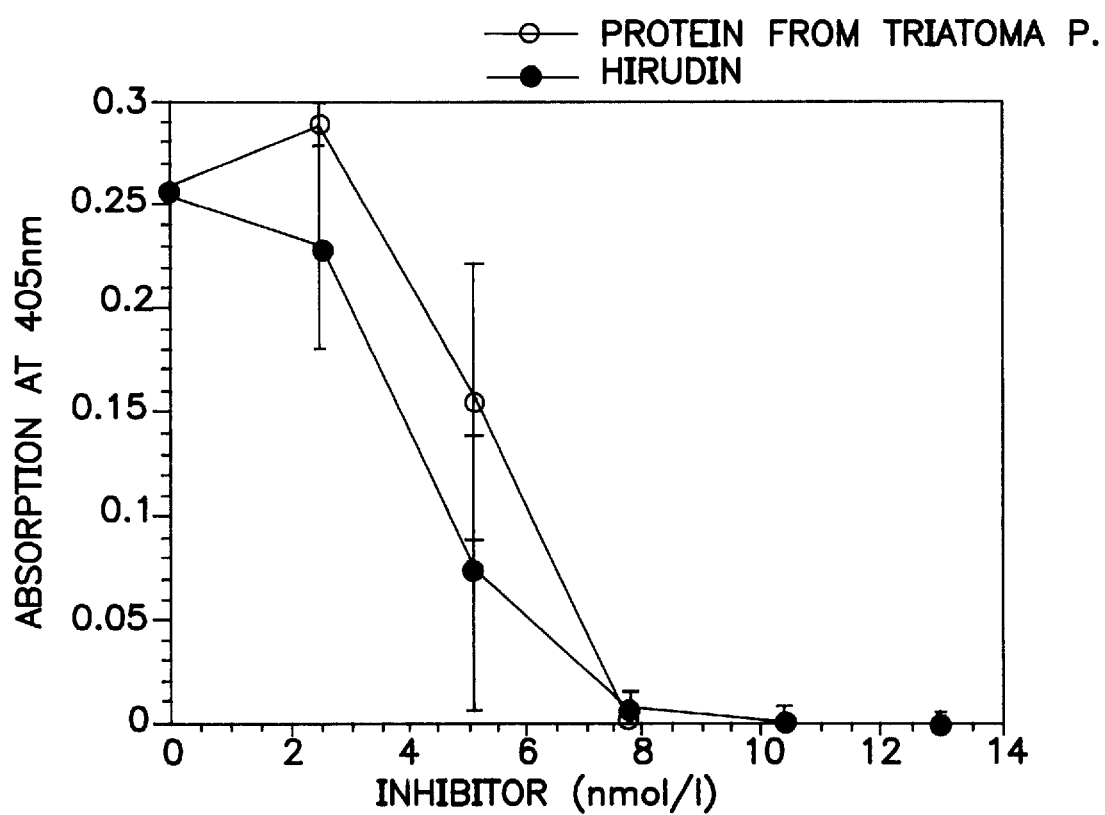

The test results are illustrated based on the figures, which show the following in detail:

FIG. 1: Lengthening of the thrombin time when adding the protein according to the invention from *Triatoma pallidipennis*, FIG. 2: Inhibition of the thrombin activity in the amidolytic test (Triatoma=thrombin inhibitor from *Triatoma pallidipennis*), FIG. 3: Inhibition of the thrombin activity in the clotting test.

EXAMPLES

Example 1

Obtaining the saliva of *Triatoma pallidipennis* and purification of the protein of the invention The cone-nosed bugs are excited by mechanical stimulation of their proboscis for secretion of their saliva. The saliva is picked up on a glass plate and collected with a siliconized, drawn-out Pasteur pipette.

The saliva is freeze-dried and dissolved in a concentration of 2.5 mg/ml in distilled water. 2 ml of this solution is gel-filtered on a "Superose 12 HR 16/50" column (Pharmacia) in 10 mmol/l of tris/HCl, pH 7.4, 0.0001% "Pluronic F68." The fractions active in the clotting test (see Example 2) are combined and applied to a CH-activated Sepharose (Pharmacia) to which thrombin previously was coupled according to the data of the manufacturer. The protein of the invention binds to this column provided with thrombin. First, the column is washed with Tyrode's buffer (without serum albumin), then it is eluted first with 10 mmol/l of Na-acetate, pH 4.5, and then with 10 mmol/l of glycine, pH 2.5. In the eluates, the pH is adjusted to 7. The 10 mmol/l of glycine eluate contains the purified protein of the invention. It is active in the clotting test (see Example 2), in the platelet aggregation test (see example 3), in the amidolytic test (see Example 4) and lengthens the thrombin time (see Example 9). The preparation contains no impurities detectable in the SDS-gel electrophoresis.

Example 2

Inhibition of the thrombin activity in the clotting test

In a microtiterplate, which is coated with bovine serum albumin (0.1% in 0.1 mol/l of NaHCO$_3$, pH 9.5), 80 $\mu$l of 20 mmol/l of HEPES, pH 7.4; 0.15 mrnol/l of NaCl; 20 $\mu$l of 20 mmol/l of CaCl$_2$; 100 $\mu$l of a diluted solution of the protein of the invention (5–50 ng) and 20 $\mu$l of thrombin (0.03 IU=0.03 International Units) are pipetted. After an incubation of 2 minutes at 37° C., 100 $\mu$l of fibrinogen (5 mg/ml) is added and incubated for 40 minutes at 37° C. Then, the absorption is measured at 405 nm. 45 ng (=8 nmol/l) of the purified protein of the invention inhibits the fibrinogen cleavage completely. Under the same test conditions, hirudin shows the same effectiveness (complete inhibition with 8 nmol/l). (See FIG. 3)

Example 3

Inhibition of the thrombin activity in the blood platelet aggregation test

500 $\mu$l of gel-filtered blood platelets (300,000/ml) is incubated with the protein of this invention (5–100 ng/ml) for 1 minute at 37° C. Then, the aggregation is induced with thrombin (0.06 IU/ml) and the aggregation is recorded in an aggregometer. Measurements with the purified protein of the invention show that at a concentration of 15 ng/ml, the aggregation is inhibited to 100%.

Example 4

Inhibition of the thrombin activity in the amidolytic test

In a microtiterplate, 80 μl of 100 mmol/l of tris/HCl, pH 7.4; 150 mmol/l of NaCl and 0.03 IU (1.35 mmol/l) of thrombin and 100 μl of a diluted solution of the protein of the invention (32–630 ng) are incubated for 10 minutes at 37° C. and then mixed with 100 μl (50 nmol) of substrate S2238 (Kabi Vitrum). After an incubation of 30 minutes at 37° C., the absorption is measured at 405 nm. 630 ng (117 nmol/l) inhibits the activity of the thrombin to approximately 50%. In a concentration of 6 nmol/l, hirudin inhibits the activity of thrombin 85%. (See FIG. 2)

Example 5

Determination of the N-terminal amino acid sequence

The purified protein of the invention was sequenced in an automatic amino acid sequenator (Applied Biosystems, Inc.) according to the instructions of the manufacturer. The sequence of amino acids 1 to 21 (of the N-terminus) is: Ala-Glu-Gly-Asp-Cys-Ser-Leu-Glu-Lys-Ala-Met-Gly-Asp-Phe-?-Pro-Glu-Glu-Phe-Phe (SEQ ID NO:18) "?" means not identifiable with complete reliability. With this amino acid, lysine is involved with the same degree of probability.

Example 6

SDS-Gel electrophoresis and determination of the molecular weight

The protein of the invention was applied in the reduced state (reduction with dithiothreitol) and in the nonreduced state together with the molecular weight markers (Electrophoresis Calibration Kit of Pharmacia), phosphorylase b (94 kDa), albumin (67 kDa), ovalbumin (43 kDa), carbonic anhydrase (30 kDa), trypsin inhibitor (20.1 kDa) and lactalbumin (14.4 kDa) to a 12.5% SDS-polyacrylamide gel and after the electrophoresis according to Laemmli (1970, Nature 227, 680–685), is stained Coomassie brilliant blue. In the reduced state, the protein of the invention travels only slightly above the trypsin inhibitor during the electrophoresis. This corresponds to a molecular weight of about 21000 Da. In the nonreduced state, the protein of the invention travels between the trypsin inhibitor and lactalbumin, which corresponds to a molecular weight of about 18000 Da.

Example 7

The protein of the invention does not inhibit serine protease factor Xa and trypsin.

The activity of factor Xa and of trypsin is measured with the following test. For factor Xa determination, 0.004 IU (0.653 pmol) of factor Xa (American Diagnostica) and 0.5 μg (28 pmol) of the protein of the invention, and for the trypsin determination, 0.004 IU (0.019 pmol) of trypsin (Sigma) and 0.016 μg (0.817 pmol) of the protein of the invention are added to 80 μl of 50 mmol/l of tris/HCl, pH 8.0, 227 mmol/l NaCl, and incubated for 2 minutes at 37° C. After adding 0.05 μmol of substrate S2222 (Kabi Vitrum), it is incubated for 20 minutes at 37° C. and then the absorption is measured at 405 nm. The absorption of these batches is just as high as that of the batches without the protein of the invention, i.e., the protein inhibits neither the activity of factor Xa nor that of trypsin.

Example 8

Isoelectric focussing

The protein of the invention is applied to a gel for isoelectric focussing in the range of pH 3 to 9 (Pharmacia) and focussed together with standard proteins (Calibration Kit pH 3 to 10 of Pharmacia). The focussing point of the protein of the invention was between that of the soybean trypsin inhibitor (I.P.=4.55) and that of β-lactoglobulin A (I.P.=5.2).

Example 9

Lengthening of the thrombin time

The thrombin time measures the activity of exogenic thrombin, which is added to the test plasma. 50 μl of solution of the protein of the invention in different dilutions (6 to 58 nmol/l ) and 50 μl of diethylbarbiturate-acetate buffer with pH 7.6 are added to 0.1 ml of plasma and incubated for 1 minute at 37° C. After adding 0.1 ml of thrombin solution (3 IU/ml), the time until the beginning of clotting is measured (Biomatic 2000 Coagulometer of Sarstedt). The protein of the invention, which is present in a concentration of 35 nmol/l, lengthens the clotting time 5-fold in comparison to a control batch. (See FIG. 1)

Example 10

Determination of internal amino acid sequences after cleavage with Lys C

The purified protein of the invention (59 μg) is reduced with 10% 2-mercaptoethanol (2 hours at room temperature under $N_2$) and then reacted with 4-vinylpyridine (2 hours at room temperature under $N_2$). After a dialysis from 25 mmol/l of tris/HCl, pH 8.5; 1 mmol/l of EDTA, the sample is mixed with 1 μg of Lys C (Boehringer Mannheim) and incubated for 6 hours at 37° C. This batch to be cleaved is applied on a Supersper RP-18, 4 μm (250×4mm, MZ-Analysentechnik [MZ Analytical Technology], Mainz) column and eluted with a gradient of 0.1% TFA in $H_2O$-0.08% TFA in 70% acetonitrile (HPLC unit of Waters). The absorption is recorded at 280 nm and at 214 nm and the eluate is fractionated. The fractions, which correspond to the absorption peak, are brought to the dried state and taken up in 30 μl of $H_2O$. Individual fractions are sequenced in an automatic amino acid sequenator (Applied Biosystems, Inc.) according to the instructions of the manufacturer. In this case, the following sequences occur (starting in each case from the N-terminus, "?" means not clearly identified):

1. Ala-Met-Gly-Asp-Phe-Lys-Pro-Glu-Glu-Phe-Phe-?-Gly-Thr-Arg(?)-Tyr-Leu-Ala (SEQ ID NO:21) (The determination of amino acid Arg is affected by uncertainty.)
2. Gly-Phe-Thr-Gln-Ile-Val-Glu-Ile-Gly-Tyr-Asn-Lys-(SEQ ID NO:21)
3. Asn-Gly-Glu-Gln-Tyr-Ser-Phe Lys-(SEQ ID NO:22)

Example 11

Molecular cloning of the cDNAs according to the invention

If the sequence of the N-terminal end of the protein according to the invention is known, a corresponding nucleotide sequence can be determined. (See WO 90/07861)

aa) Production of specific samples in the PCR

To determine the cDNA according to the invention, first the primer (model, priming piece) is synthesized, which is derived from the amino acid sequence previously determined in the Edman degradation. The synthesized oligonucleotide sequences of the primer are used to amplify a fragment of the cDNA according to the invention with the PCR (polymerase chain reaction). (See U.S. Pat. No. 4,800, 159)

Two oligonucleotide primers are produced by the nucleotide sequence being derived from the previously partially determined amino acid sequence of the N-terminal area of the complete protein according to the invention and of one of its fragments. In this case, the following amino acid sequences are used:

N-terminal sequence of the complete protein:

Ala—Glu—Gly—Asp—Asp—Cys—Ser—Leu—Glu—Lys—
        5                                10
Ala—Met—Gly—Asp—Phe (SEQ ID NO:17)
        15 and N-terminal sequence of the fragment:

Gly—Phe—Thr—Gln—Ile—Val—Glu—Ile—Gly—Tyr—
        5                            10
Asn—Lys (SEQ ID NO:21)
   12

The template consists of the cDNA, which is derived from a poly-A$^+$-RNA, which was previously isolated from the salivary glands of *Triatoma pallidipennis*. (SAMBROCK et al.: Molecular Cloning (Chapter 7, pp. 18–22, Cold Spring Harbor Laboratory Press, 1989)

Template priming piece (sense primer): 5'-GCI GA(A/G) GGI GA(C/T) GA (C/T) TG (C/T) TCI CTI GA(A/G) AA(A/G) GCI ATG GGI GA(C/T) TT-3' (SEQ ID NO:23)

Non-template-priming piece (antisense primer):
5'-TT (G/A)TT (G/A)TA ICC (G/A)AT (T/C)TC IAC (G/A)AT (T/C)TG IGT (G/A)AA-3 (SEQ ID NO:24)
A=deoxyadenosine; C=deoxycytidine;
G=deoxyguanosine; T=deoxythymidine and
I=deoxyinosine The PCR consists of 40 cycles. A cycle appears as follows:
a) 2 minutes of denaturation at 94° C.,
b) 90 seconds of hybridization at 52° C. and
c) 2 minutes of lengthening at 72° C.

The PCR replication product obtained by the previously described process exhibits a band on an agarose gel. The latter is isolated from the agarose gel, which exhibits a low melting point, and directly conveyed to the PCR plasmid (Stratagene) and subcloned. The process corresponds to the description of the protocol of the manufacturer (PCR-Script™ SK(+) cloning kit of Stratagene). The DNA sequence of the insertion product corresponds to the sequence of the PCR product and is determined as it is described in SANGER et al. Proc Natl Acad Sci USA (1977) 74: 5463–5467.

bb) Selection process of the cDNA bank and isolation of the cDNA clone according to the invention.

About 400,000 primary clones from the salivary gland-cDNA bank of *T. pallidipennis* (cDNA library) are transferred on nylon membranes (Pall Biosupport East Hills, N.Y., USA) and screened, as the manufacturer stipulates. A marked sample, which was obtained with the help of the previously described PCR replication method is used in this case. The selection process is performed twice, followed by a conversion of phage-DNA to plasmid-DNA and a sequential analysis of the insert (incorporated DNA) of this plasmid. As a result, four cDNA sequences are determined, which are pictured in sequence identifiers 13 to 16, in which only the triplicates for amino acids −17 to −9 in the case of Ti28 and Ti45 and the triplicate for amino acid −18 in the case of Ti12 are missing.

Every two strands of the isolated DNA are sequenced. The amino acid sequence derived from the coding DNA is completely identical with the amino acid sequence, which was previously discovered by the Edman degradation of the protein purified according to the invention.

The longest cDNA clone (Ti12) begins with nucleotides TG, which correspond to an incomplete priming codon for methionine. This is obvious when an additional isolated clone (Ti5) is taken into consideration, which was found with a selection process with 600,000 phages of the same cDNA bank, which was used in the selection of Ti12, Ti28 and Ti45.

TABLE 2

Positions, in which the proteins according to the invention have differences.

|  |  | Clone Klon | | | |
| --- | --- | --- | --- | --- | --- |
|  |  | Ti5 | Ti12 | Ti28 | Ti45 |
| Position | 8 | Ile | Leu | Leu | Leu |
| Position | 32 | Gly | Gly | Asp | Asp |
| Position | 72 | Val | Val | Val | Ala |
| Position | 74 | Asn | Asn | Asn | Lys |
| Position | 77 | Gly | Asp | Asp | Asp |
| Position | 86 | Ser | Gly | Gly | Gly |
| Position | 114 | Thr | Ile | Ile | Thr |
| Position | 127 | Leu | Phe | Phe | Phe |
| Position | 139 | Lys | Asn | Asn | Asn |

The four cDNA sequences of the protein according to the invention are selected, identified and sequenced according to the previously described methods. Only 9 positions exhibit differences in the derived amino acid sequence. The differences are listed in Table 2.

The identity and similarilty of the four mature proteins according to the invention is about 95 or 98%, depending on which comparison partner is selected.

Example 12

Production of a plasmid coding the protein according to the invention and expression and purification of the protein produced in *E. Coli*

If the DNA sequences are known, matching promoters and optionally matching enhancers can be connected with the respective DNA sequences, so that then a usable vector is present. (M. WIRTH, L. SCHUMACHER and H. HAUSER, in H. S. CONRADT (ed) Protein Glycosylation, Cellular Biotechnical and Analytical Aspects Vol. 15, 49–52, VCH publishers, Weinheim, 1991); also J. KRATZSCHMAR et al. (1992) Genes 116: 281–284. The expression of such a vector is possible in eukaryotes (for example, baby hamster kidney cells). Further, the DNA sequences can be incorporated in matching prokaryotic vectors for expression in *E. coli* strains.

a) Production of plasmid
  i) Introduction

The construct for expression of the recombinant protein according to the invention in prokaryotes is produced by the commercially available plasmid pKK233-2 being used, which contains the IPTG-inducible trc promoter. The vector suitable for expression comprises this plasmid pKK233-2, in which both the coding sequence of the protein according to the invention and a signal sequence are inserted. The signal sequence is a modified signal sequence, which is attributable to the secreted *E. coli* protein cyclophilin a. The signal sequence and the coding DNA is downstream from the promoter, by which the pKK/cph develops (T. HAYANO 1991) Biochemistry 30: 3041–3048).

The coding sequences of the protein according to the invention are inserted in the expression plasmid and the thus obtained construct (pKK/cph-protein) is used for the transformation of competent *E. coli* JM 105 cells.

(ii) Structure of the plasmid pKK/cph
The following pair of partially overlapping and complementary oligodeoxynucleotides is used to recover the coding DNA for the signal sequence of cyclophilin a. In this case, the corresponding C-terminal end of the cyclophilin sequence is modified to form an optimum cleavage point for the bacterial signal peptidase. The modification consists in the fact that the last seven triplicates of the C-terminal end are exchanged for triplicates which code the following amino acid sequence: Phe-Ser-Ala-Ser-Ala-Leu-Ala (SEQ ID NO:25) (R. E. DALBEY and G. von HEIJNE (1992) TIBS 17: 474–478).

Sense-bearing oligonucleotide sequence: (sense oligo)

5'-GCGATAACAT GTTCAAAAGC ACCCTGGCGG CGATGGCTGC TGTTTTCGCT CTGTCTG-3'; (SEQ ID NO:26)

Non-sense-bearing oligonucleotide sequence: (antisense oligo)

5'-CGCTATAAGC TTCTGCAGGC TAGCGCGCTC GCGCTGAAAG CAGACACAGT CGAAACAG-3' (SEQ ID NO:27)

After the addition of the starter sequence and the subsequent completion of the daughter pieces by use of the Taq polymerase, the DNA fragments are cleaved with AflIII and HindIII. The cleavage points are underlined. Then, the DNA fragment between the NcoI and HindIII point of plasmid pKK233–2 is subcloned. The NheI point, which together with the HindIII point facilitates the further subcloning of cDNA pieces, is made known by bold print.

(ii) Structure of the plasmid with the protein according to the invention

The following pair of starting sequences (primer) is used to duplicate the coding sequence for the mature protein according to the invention (Ti28=seq. id. no. 2). In this case, the NheI and HindIII interfaces, which are underlined, are required for insertion in the plasmid pKK/cph.

Sense-bearing oligonucleotide sequence: (sense oligo)

5'-GCGATAGCTA GCAGCAGAAG GTGACGAC-3' (SEQ ID NO:28);

Non-sense-bearing oligonucleotide sequence: (antisense oligo)

5,-GCGATAGGAT CCAAGCTTAC TAACAAATTT CATTAGCATC AGG-3' (SEQ ID NO:29)

Ten cycles consisting of 2 minutes at 94° C., 2 minutes at 30° C. and 2.5 minutes at 72° C. are performed for the PCR (polymerase chain reaction), in which 2 μg template strands (templates) are used. The duplicated DNA is isolated on a low-boiling agarose gel, cleaved with NheI and HindIII and conveyed to the plasmid pKK/cph, which was previously cleaved with the same restriction endonucleases. The thus obtained construct is examined with the help of a total sequencing of the coding DNA and the DNA flanking the coding DNA.

(iii) Transformation of E. coli.

E. coli JM 105 cells are transformed with the use of the $CaCl_2$ process. In this case, 1 μg of pKK/cph DNA, which codes the protein according to the invention, is used.

b) Purification and characterization of the protein according to the invention produced with E. coli A culture of the transformed E. coli cells is mixed with IPTG (1 mmol/l) and incubated for six hours at 37° C. (IPTG=isopropyl-β-D-thiogalactoside). The cells are centrifuged off and subjected to an osmotic shock (saccharose and subsequent $H_2O$ treatment). The thus obtained periplasma fraction inhibits the activity of thrombin in the clotting test (Comparison Example 2). The inhibitory activity is purified by ion exchange chromatography on DE-52 cellulose and thrombin affinity chromatography. (comparison Example 1)

The purified fraction has the same inhibitory activity as the saliva protein. It shows identical behavior in an SDS-polyacrylamide electrophoresis (Comparison Example 6). Further, it is identical in the N-terminal amino acid sequence with the mature saliva protein.

---

We claim:

1. An isolated mature protein having the N-terminal amino acid sequence:

(SEQ ID NO:19)
a) Ala—Glu—Gly—Asp—Asp—Cys—Ser—Leu—Glu—Lys—
                           5                10
Ala—Met—Gly—Asp—Phe—Lys—Pro—Glu—Glu—Phe—Phe,
                   15                 20 or b) an allelic variant of an N-terminal sequence of SEQ ID NO:19 wherein 1 or 2 amino acids of SEQ ID NO:19 are substituted, deleted or inserted without significantly affecting the activity of the protein, or c) a sequence of SEQ ID NO:19 or an allelic variant as in b), further having a posttranslational modification which does not substantially affect the activity of the mature protein, wherein said protein inhibits mammalian thrombin.

2. An isolated mature protein which inhibits mammalian thrombin, having an amino acid sequence selected from:

a) the sequence in SEQ ID NO:1, 2, 3 or 4; or b) a sequence comprising an allelic variant of a sequence of SEQ ID NO:1, 2, 3 or 4; or c) a sequence of SEQ ID NO:1, 2, 3 or 4 or an allelic variant as in b), further having a posttranslational modification which does not substantially affect the activity of the mature protein.

3. An isolated preprotein, comprising an N-terminal signal peptide sequence operably linked to a mature protein of claim 1.

4. An isolated preprotein, comprising an N-terminal signal peptide sequence operably linked to a mature protein of claim 2.

5. A preprotein of claim 4, having an amino acid sequence selected from:

a) the sequence in SEQ ID NO:5, 6, 7 or 8; or b) a sequence comprising an allelic variant of a sequence in SEQ ID NO:5, 6, 7 or 8; or c) a sequence of SEQ ID NO:5, 6, 7 or 8 or an allelic variant as in b), further having a posttranslational modification which does not substantially affect the activity of the mature protein.

6. A protein of claim 1, which is recombinantly produced.

7. A protein of claim 2, which is recombinantly produced.

8. A preprotein of claim 3, which is recombinantly produced.

9. A preprotein of claim 5, which is recombinantly produced.

10. A protein of claim 1, which is glycosylated.

11. A protein of claim 2, which is glycosylated.

12. A preprotein of claim 3, which is glycosylated.

13. A preprotein of claim 5, which is glycosylated.

14. An isolated cDNA or DNA which encodes a mature thrombin inhibitor protein of claim 2, having a DNA sequence selected from:

a) the sequence in SEQ ID NO:9, 10, 11 or 12; or b) a sequence comprising an allelic variant of a sequence in SEQ ID NO:9, 10 11 or 12;

wherein said mature protein encoded thereby inhibits mammalian thrombin.

15. An isolated cDNA or DNA which encodes a preprotein comprising an N-terminal signal peptide sequence operably linked to a mature thrombin inhibitor protein encoded by a DNA of claim 14, having a DNA sequence selected from:

a) the sequence in SEQ ID NO:13, 14, 15 or 16; or b) a sequence comprising an allelic variant of a sequence in SEQ ID NO:13, 14, 15 or 16;

wherein said mature protein encoded thereby inhibits mammalian thrombin.

16. A vector comprising a cDNA or DNA of claim 14, operably linked to a promoter and optionally to an enhancer.

17. A vector comprising a cDNA or DNA of claim 16, operably linked to a promoter and optionally to an enhancer.

18. A eukaryotic or procaryotic host cell, transformed with a vector of claim 16.

19. A eukaryotic or procaryotic host cell, transformed with a vector of claim 17.

20. A process for the production of a mature thrombin inhibitor protein, comprising:

cultivating a host cell transformed with a vector of claim 16 under conditions suitable for expression of the protein, and isolating and purifying the protein.

21. A process for the production of a thrombin inhibitor protein, comprising:

cultivating a host cell transformed with a vector of claim 17 under conditions suitable for expression of the protein, isolating and purifying the protein, and, optionally, removing the signal peptide.

22. A process of claim 20, wherein the protein is isolated, purified on at least one column and then concentrated by evaporation.

23. A process for the purification of a mature thrombin inhibitor protein of claim 1, comprising:

applying a crude mixture containing said inhibitor to a an agarose gel filtration chromatography column, eluting protein from said column, applying the eluate having thrombin inhibitor activity to a CH-activated chromatography column to which thrombin was previously coupled, and eluting the purified inhibitor protein.

24. A process of claim 23, wherein the crude mixture is the saliva of *Triatoma pallidipennis*.

25. A process for the purification of a mature thrombin inhibitor protein, comprising:

applying a crude mixture containing said inhibitor to an agarose gel filtration chromatography column, eluting protein from said column, applying the eluate having thrombin inhibitor activity to a CH-activated chromatography column to which thrombin was previously coupled, and eluting the purified inhibitor protein, wherein the crude mixture is derived from a host cell transformed with a vector comprising a cDNA or DNA molecule of claim 14 operably linked to a promoter and optionally to an enhancer.

26. A pharmaceutical composition, comprising a protein of claim 1 and a pharmaceutically acceptable excipient.

27. A pharmaceutical composition, comprising a protein of claim 2 and a pharmaceutically acceptable excipient.

28. A method of treating thromboses or unstable angina or arteriosclerosis, preventing a reblockage of vessels after angioplasty with a balloon catheter or preventing blood clotting in hemodialysis, comprising administering to a patient in need thereof an effective amount of a thrombin inhibitor of claim 1.

29. A method of treating thromboses or unstable angina or arteriosclerosis, preventing a reblockage of vessels after angioplasty or preventing blood clotting during hemodialysis, comprising administering to a patient in need of such treatment an effective amount of a thrombin inhibitor of claim 2.

* * * * *